United States Patent
Juergens et al.

(10) Patent No.: US 11,389,226 B2
(45) Date of Patent: *Jul. 19, 2022

(54) SURGICAL INSTRUMENTS AND SYSTEMS WITH MULTIMODES OF TREATMENTS AND ELECTROSURGICAL OPERATION

(71) Applicant: Cynosure, LLC, Westford, MA (US)

(72) Inventors: Albert M. Juergens, Boylston, MA (US); Frank D'Amelio, Los Olivos, CA (US)

(73) Assignee: Cynosure, LLC, Westford, MA (US)

( * ) Notice: Subject to any disclaimer, the term of this patent is extended or adjusted under 35 U.S.C. 154(b) by 390 days.

This patent is subject to a terminal disclaimer.

(21) Appl. No.: 16/684,937

(22) Filed: Nov. 15, 2019

(65) Prior Publication Data

US 2020/0093533 A1 Mar. 26, 2020

Related U.S. Application Data

(63) Continuation of application No. 14/214,627, filed on Mar. 14, 2014, now Pat. No. 10,492,849.
(Continued)

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1477* (2013.01); *A61B 2018/00464* (2013.01);
(Continued)

(58) Field of Classification Search
CPC . A61B 18/1233; A61B 18/1477; A61B 18/16; A61B 2018/00464;
(Continued)

(56) References Cited

U.S. PATENT DOCUMENTS

| 236,203 A | 1/1881 | Campbell |
| 1,881,250 A | 10/1932 | Tomlinson |

(Continued)

FOREIGN PATENT DOCUMENTS

| CN | 1697631 | 11/2005 |
| CN | 101610736 | 12/2009 |

(Continued)

OTHER PUBLICATIONS

Examination Report in Australian Application No. 2019217623, dated Mar. 10, 2021, 4 pages.
(Continued)

*Primary Examiner* — Adam Marcetich
(74) *Attorney, Agent, or Firm* — Ganz Pollard, LLC

(57) ABSTRACT

In some embodiments, the inventive subject matter is directed to a multimode electrosurgical system having an electrosurgical instrument with a first electrode configuration that operates in a bipolar mode and second electrode configuration that operates in a monopolar mode. In other embodiments, the inventive subject matter is directed to an instrument and system that provide multiple modes of surgical and/or therapeutic treatments, at least one being an electrosurgical mode of treatment, the instrument including at least one active electrode on a working portion, and the working portion including or supporting at least one non-electrosurgical functional element, the instrument including at least one operational return electrode configuration of selectively variable surface area.

29 Claims, 5 Drawing Sheets

Related U.S. Application Data

(60) Provisional application No. 61/794,732, filed on Mar. 15, 2013.

(51) Int. Cl.
*A61B 18/20* (2006.01)
*A61B 18/00* (2006.01)
*A61B 18/16* (2006.01)
*A61N 1/32* (2006.01)

(52) U.S. Cl.
CPC .............. *A61B 2018/00642* (2013.01); *A61B 2018/00678* (2013.01); *A61B 2018/00708* (2013.01); *A61B 2018/00791* (2013.01); *A61B 2018/00982* (2013.01); *A61B 2018/00994* (2013.01); *A61B 2018/124* (2013.01); *A61B 2018/126* (2013.01); *A61B 2018/1253* (2013.01); *A61B 2018/1407* (2013.01); *A61B 2018/1467* (2013.01); *A61B 2018/1497* (2013.01); *A61B 2018/162* (2013.01); *A61B 2018/165* (2013.01); *A61B 2018/20361* (2017.05); *A61N 1/328* (2013.01)

(58) Field of Classification Search
CPC .......... A61B 2018/00642; A61B 2018/00708; A61B 2018/00791; A61B 2018/124; A61B 2018/1253; A61B 2018/126; A61B 2018/1407; A61B 2018/1467; A61B 2018/1497; A61B 2018/162; A61B 2018/165; A61B 2018/20361
See application file for complete search history.

(56) References Cited

U.S. PATENT DOCUMENTS

| | | | |
|---|---|---|---|
| 1,916,722 A | 7/1933 | Ende | |
| 1,942,543 A | 1/1934 | Forman | |
| 1,943,543 A | 1/1934 | McFadden | |
| 1,945,327 A | 1/1934 | Morse | |
| 1,983,669 A | 12/1934 | Kimble | |
| 2,102,270 A | 12/1937 | Hyams | |
| 2,888,928 A | 6/1959 | Seiger | |
| 3,058,470 A | 10/1962 | Seeliger et al. | |
| 3,532,095 A | 10/1970 | Miller et al. | |
| 3,730,188 A | 5/1973 | Ellman | |
| 3,799,168 A | 3/1974 | Peters | |
| 3,825,004 A | 7/1974 | Durden | |
| 3,825,044 A | 7/1974 | Lidikay et al. | |
| 3,858,586 A | 1/1975 | Lessen | |
| 3,879,947 A | 4/1975 | Gaiser | |
| 3,916,909 A | 11/1975 | Kletschka et al. | |
| 3,920,022 A | 11/1975 | Pastor | |
| D246,053 S | 10/1977 | Staub et al. | |
| 4,051,855 A | 10/1977 | Schneiderman | |
| 4,071,028 A | 1/1978 | Perkins | |
| 4,103,688 A | 8/1978 | Edwards | |
| 4,108,182 A | 8/1978 | Hartman et al. | |
| 4,123,673 A | 10/1978 | Gonser | |
| 4,137,919 A | 2/1979 | Farin et al. | |
| 4,148,321 A | 4/1979 | Wyss | |
| 4,148,324 A | 4/1979 | Muller et al. | |
| 4,171,700 A | 10/1979 | Farin | |
| 4,188,927 A | 2/1980 | Harris | |
| 4,221,222 A | 9/1980 | Detsch | |
| 4,185,927 A | 10/1980 | Uttech | |
| 4,246,902 A | 1/1981 | Martinez | |
| 4,271,891 A | 1/1981 | Pommier | |
| 4,269,174 A | 5/1981 | Adair | |
| 4,271,837 A | 6/1981 | Aesculap-Werke | |
| 4,289,132 A | 9/1981 | Rieman | |
| 4,312,364 A | 1/1982 | Convert et al. | |
| 4,314,560 A | 2/1982 | Helfgott | |
| D263,872 S | 4/1982 | Rakocy et al. | |
| 4,334,539 A | 6/1982 | Childs et al. | |
| 4,346,416 A | 8/1982 | Riggle et al. | |
| 4,378,801 A | 4/1983 | Oosten | |
| 4,438,766 A | 3/1984 | Bowers | |
| 4,463,759 A | 8/1984 | Garito | |
| 4,473,075 A | 9/1984 | Rexroth | |
| 4,476,862 A | 10/1984 | Pao | |
| 4,492,231 A | 1/1985 | Auth | |
| 4,517,975 A | 5/1985 | Garito | |
| 4,550,727 A | 5/1985 | Rexroth | |
| 4,541,440 A | 9/1985 | Parsonnet | |
| 4,548,207 A | 10/1985 | Reimels | |
| D281,721 S | 12/1985 | Scanlan | |
| 4,557,272 A | 12/1985 | Carr | |
| 4,565,200 A | 1/1986 | Cosman | |
| 4,658,815 A | 4/1987 | Farin et al. | |
| 4,658,819 A | 4/1987 | Harris | |
| 4,658,820 A | 4/1987 | Klicek | |
| 4,688,569 A | 8/1987 | Rabinowitz | |
| 4,701,193 A | 10/1987 | Robertson et al. | |
| 4,706,667 A | 11/1987 | Roos | |
| 4,711,239 A | 12/1987 | Sorochenko et al. | |
| 4,712,544 A | 12/1987 | Ensslin | |
| 4,716,897 A | 1/1988 | Noguchi et al. | |
| 4,754,754 A | 7/1988 | Garito | |
| 4,821,717 A | 4/1989 | Wehrli | |
| 4,827,927 A | 5/1989 | Newton | |
| 4,834,095 A | 5/1989 | Miller | |
| 4,886,060 A | 12/1989 | Wiksell | |
| 4,892,105 A | 1/1990 | Prass | |
| 4,931,047 A | 6/1990 | Broadwin et al. | |
| 4,936,281 A | 6/1990 | Stasz | |
| 4,962,766 A | 10/1990 | Herzon | |
| 4,986,839 A | 1/1991 | Wertz et al. | |
| 5,035,695 A | 7/1991 | Weber | |
| D320,271 S | 9/1991 | Jones | |
| 5,047,026 A | 9/1991 | Rydell | |
| 5,047,029 A | 9/1991 | Aebi et al. | |
| D320,856 S | 10/1991 | Scheller | |
| D321,056 S | 10/1991 | Chambers | |
| 5,067,953 A | 11/1991 | Feucht | |
| D322,483 S | 12/1991 | Kishimoto | |
| D322,676 S | 12/1991 | Chambers | |
| 5,078,716 A | 1/1992 | Doll | |
| 5,098,430 A | 3/1992 | Fleenor | |
| 5,125,058 A | 6/1992 | Tenerez et al. | |
| 5,127,460 A | 7/1992 | Abadi et al. | |
| D329,718 S | 9/1992 | Sulik | |
| 5,160,334 A | 11/1992 | Billings et al. | |
| 5,186,714 A | 2/1993 | Boudreault et al. | |
| 5,195,959 A | 3/1993 | Smith | |
| 5,196,007 A | 3/1993 | Ellman | |
| 5,217,458 A | 6/1993 | Parins | |
| 5,217,460 A | 6/1993 | Knoepfler | |
| 5,261,905 A | 6/1993 | Doresey | |
| 5,224,947 A | 7/1993 | Cooper | |
| 5,226,939 A | 7/1993 | Nicolas et al. | |
| 5,243,812 A | 9/1993 | Strobel et al. | |
| 5,246,440 A | 9/1993 | Van Noord | |
| 5,267,994 A | 12/1993 | Gentelia et al. | |
| 5,267,998 A | 12/1993 | Hagen | |
| 5,275,151 A | 1/1994 | Shockey et al. | |
| 5,281,218 A | 1/1994 | Imran | |
| 5,290,283 A | 3/1994 | Suda | |
| 5,304,183 A | 4/1994 | Gourlay et al. | |
| D346,866 S | 5/1994 | Lotuaco | |
| 5,318,563 A | 6/1994 | Malis et al. | |
| 5,324,288 A | 6/1994 | Billings et al. | |
| 5,325,288 A | 6/1994 | Satou | |
| 5,342,349 A | 8/1994 | Kaufman | |
| 5,342,356 A | 8/1994 | Ellman | |
| D351,227 S | 10/1994 | Patton et al. | |
| D352,350 S | 11/1994 | Rambo et al. | |
| 5,336,218 A | 11/1994 | Linhares | |
| 5,360,428 A | 11/1994 | Hutchinson | |
| 5,364,393 A | 11/1994 | Auth et al. | |
| 5,368,560 A | 11/1994 | Rambo et al. | |
| 5,374,188 A | 12/1994 | Frank et al. | |
| 5,380,245 A | 1/1995 | Reiterman et al. | |

(56) References Cited

U.S. PATENT DOCUMENTS

| | | |
|---|---|---|
| 5,383,923 A | 1/1995 | Webster, Jr. |
| 5,396,893 A | 3/1995 | Oberg |
| 5,403,311 A | 4/1995 | Abele et al. |
| 5,413,574 A | 5/1995 | Fugo |
| 5,423,779 A | 7/1995 | Shimo et al. |
| 5,437,664 A | 8/1995 | Cohen et al. |
| 5,441,499 A | 8/1995 | Fritzsch |
| 5,456,683 A | 10/1995 | Fritzsch et al. |
| 5,458,597 A | 10/1995 | Edwards et al. |
| 5,456,248 A | 11/1995 | Fuji |
| 5,465,248 A | 11/1995 | Fuji |
| 5,478,303 A | 12/1995 | Foley-Nolen |
| 5,505,728 A | 4/1996 | Ellman |
| 5,514,131 A | 5/1996 | Edwards |
| 5,562,503 A | 10/1996 | Ellman |
| 5,571,101 A | 11/1996 | Ellman et al. |
| D376,423 S | 12/1996 | Monea |
| 5,594,686 A | 1/1997 | Hazen et al. |
| 5,599,347 A | 2/1997 | Hart et al. |
| 5,613,966 A | 3/1997 | Makower et al. |
| 5,620,441 A | 4/1997 | Gref et al. |
| 5,636,733 A | 6/1997 | Marchwiak |
| D382,342 S | 8/1997 | Rosen |
| 5,662,680 A | 9/1997 | Desai |
| 5,679,401 A | 10/1997 | Bawden |
| 5,683,387 A | 11/1997 | Garito |
| 5,685,878 A | 11/1997 | Falwell et al. |
| D388,170 S | 12/1997 | Sjostrom |
| 5,709,675 A | 1/1998 | Williams |
| 5,713,942 A | 2/1998 | Stern et al. |
| D393,067 S | 3/1998 | Geary et al. |
| 5,733,282 A | 3/1998 | Ellman et al. |
| D393,715 S | 4/1998 | Strickland |
| 5,735,846 A | 4/1998 | Panescu et al. |
| 5,741,250 A | 4/1998 | Garito |
| 5,746,746 A | 5/1998 | Garito |
| 5,755,716 A | 5/1998 | Garito |
| 5,766,171 A | 6/1998 | Silvestrini |
| 5,769,702 A | 6/1998 | Hanson |
| 5,807,392 A | 9/1998 | Eggers |
| 5,814,044 A | 9/1998 | Hooven |
| 5,833,689 A | 11/1998 | Long |
| 5,836,897 A | 11/1998 | Sakurai et al. |
| D402,030 S | 12/1998 | Roberts et al. |
| 5,871,524 A | 2/1999 | Knowlton |
| 5,891,142 A | 4/1999 | Eggers |
| D409,335 S | 5/1999 | Slater |
| 5,916,158 A | 6/1999 | Webster, Jr. |
| 5,924,206 A | 7/1999 | Cote et al. |
| 5,925,039 A | 7/1999 | Landingham |
| 5,948,009 A | 9/1999 | Tu |
| 5,954,686 A | 9/1999 | Garito |
| 5,984,918 A | 11/1999 | Garito |
| 5,993,447 A | 11/1999 | Blewett et al. |
| D417,371 S | 12/1999 | Searle et al. |
| 5,997,533 A | 12/1999 | Kuhns |
| 5,997,733 A | 12/1999 | Wilbur et al. |
| 6,001,077 A | 12/1999 | Ellman |
| 6,006,755 A | 12/1999 | Edwards |
| 6,010,500 A | 1/2000 | Sherman et al. |
| 6,039,734 A | 3/2000 | Goble |
| 6,044,846 A | 4/2000 | Edwards |
| 6,050,993 A | 4/2000 | Tu et al. |
| 6,059,734 A | 5/2000 | Yoon |
| 6,063,085 A | 5/2000 | Tay et al. |
| 6,068,628 A | 5/2000 | Fanton et al. |
| 6,080,152 A | 6/2000 | Nardella et al. |
| D428,146 S | 7/2000 | Svanberg et al. |
| 6,093,186 A | 7/2000 | Goble |
| D422,024 S | 8/2000 | Amdrews et al. |
| 6,102,046 A | 8/2000 | Weinstein et al. |
| 6,113,596 A | 9/2000 | Hooven et al. |
| 6,123,702 A | 9/2000 | Swanson et al. |
| D431,972 S | 10/2000 | Naft et al. |
| 6,156,032 A | 12/2000 | Lennox |
| 6,159,194 A | 12/2000 | Eggers et al. |
| 6,203,762 B1 | 3/2001 | Skalla et al. |
| 6,206,842 B1 | 3/2001 | Tu |
| D441,007 S | 4/2001 | Garito et al. |
| D441,077 S | 4/2001 | Garito et al. |
| 6,214,003 B1 | 4/2001 | Morgan et al. |
| 6,228,078 B1 | 5/2001 | Eggers et al. |
| 6,228,084 B1 | 5/2001 | Kirwan, Jr. |
| 6,231,571 B1 | 5/2001 | Ellman |
| 6,235,027 B1 | 5/2001 | Herzon |
| 6,238,388 B1 | 5/2001 | Ellman et al. |
| 6,238,394 B1 | 5/2001 | Garito |
| 6,245,068 B1 | 6/2001 | Olson et al. |
| 6,251,110 B1 | 6/2001 | Wampler |
| 6,280,441 B1 | 8/2001 | Ryan |
| 6,296,637 B1 | 10/2001 | Thorne et al. |
| 6,312,428 B1 | 11/2001 | Eggers et al. |
| D453,222 S | 1/2002 | Garito |
| 6,348,051 B1 | 2/2002 | Farin et al. |
| 6,355,032 B1 | 3/2002 | Hovda et al. |
| 6,368,324 B1 | 4/2002 | Dinger et al. |
| 6,387,092 B1 | 5/2002 | Burnside et al. |
| 6,387,093 B1 | 5/2002 | Ellman et al. |
| 6,395,001 B1 | 5/2002 | Ellman et al. |
| 6,402,742 B1 | 6/2002 | Blewet et al. |
| 6,409,726 B1 | 7/2002 | Ellman |
| 6,413,255 B1 | 7/2002 | Stern |
| 6,416,512 B1 | 7/2002 | Ellman et al. |
| 6,417,532 B2 | 7/2002 | Tsunoda et al. |
| 6,432,105 B1 | 8/2002 | Ellman |
| 6,447,509 B1 | 9/2002 | Bonnet et al. |
| 6,461,352 B2 | 10/2002 | Morgan et al. |
| 6,506,267 B1 | 1/2003 | Fujiyasu et al. |
| 6,517,532 B1 | 2/2003 | Altshuler et al. |
| 6,530,924 B1 | 3/2003 | Ellman |
| 6,540,745 B1 | 4/2003 | Fairbourn et al. |
| 6,544,210 B1 | 4/2003 | Trudel et al. |
| 6,546,935 B2 | 4/2003 | Hooven |
| 6,562,032 B1 | 5/2003 | Ellman |
| 6,562,036 B1 | 5/2003 | Ellman |
| 6,565,561 B1 | 5/2003 | Goble et al. |
| 6,572,613 B1 | 6/2003 | Ellman et al. |
| 6,582,427 B1 | 6/2003 | Goble |
| 6,585,791 B1 | 7/2003 | Garito et al. |
| 6,592,580 B1 | 7/2003 | Stockert |
| 6,605,080 B1 | 8/2003 | Altshuler et al. |
| 6,607,528 B1 | 8/2003 | Quick et al. |
| 6,613,047 B2 | 9/2003 | Edwards |
| 6,613,048 B2 | 9/2003 | Mulier et al. |
| D481,841 S | 11/2003 | Hsu |
| 6,652,514 B2 | 11/2003 | Ellman |
| 6,663,620 B2 | 12/2003 | Altshuler et al. |
| 6,673,072 B1 | 1/2004 | Garito et al. |
| 6,679,881 B1 | 1/2004 | Bybee |
| 6,689,071 B2 | 2/2004 | Burbank et al. |
| 6,730,323 B1 | 5/2004 | Murley et al. |
| 6,749,608 B2 | 6/2004 | Garito |
| 6,759,624 B2 | 6/2004 | Knowlton |
| 6,766,202 B2 | 7/2004 | Underwood et al. |
| 6,767,348 B2 | 7/2004 | Nakada et al. |
| D494,270 S | 8/2004 | Reschke |
| 6,802,842 B2 | 10/2004 | Ellman |
| D500,168 S | 12/2004 | Ho |
| 6,830,569 B2 | 12/2004 | Thompson et al. |
| D500,854 S | 1/2005 | Eichel |
| 6,837,884 B2 | 1/2005 | Woloszko |
| 6,892,580 B2 | 5/2005 | Pankey et al. |
| 6,920,883 B2 | 7/2005 | Bessette et al. |
| 6,926,717 B1 | 8/2005 | Garito |
| D510,138 S | 9/2005 | Kim |
| D510,158 S | 9/2005 | Cheung |
| 6,974,451 B2 | 12/2005 | Altshuler et al. |
| 6,976,985 B2 | 12/2005 | Altshuler et al. |
| 6,994,707 B2 | 2/2006 | Ellman |
| 7,070,604 B1 | 7/2006 | Garito |
| 7,090,649 B2 | 8/2006 | Kang |
| 7,094,231 B1 | 8/2006 | Ellman et al. |
| D533,943 S | 12/2006 | Chen |
| 7,147,634 B2 | 12/2006 | Nesbitt |

(56) References Cited

U.S. PATENT DOCUMENTS

| | | |
|---|---|---|
| D535,397 S | 1/2007 | Chen |
| 7,156,844 B2 | 1/2007 | Reschke et al. |
| 7,160,295 B1 | 1/2007 | Garito |
| 7,163,336 B2 | 1/2007 | Blakeley, III |
| D538,936 S | 3/2007 | Bohmel et al. |
| D548,843 S | 8/2007 | Kertz |
| 7,258,689 B2 | 8/2007 | Russell |
| 7,276,058 B2 | 10/2007 | Altshuler et al. |
| D555,803 S | 11/2007 | Garito |
| 7,351,252 B2 | 4/2008 | Altshuler et al. |
| 7,422,586 B2 | 9/2008 | Morris et al. |
| 7,427,289 B2 | 9/2008 | Sierra et al. |
| 7,473,251 B2 | 1/2009 | Knowlton et al. |
| 7,479,140 B2 | 1/2009 | Ellman |
| 7,507,232 B1 | 3/2009 | Garito |
| D591,365 S | 4/2009 | Pasko et al. |
| 7,572,251 B1 * | 8/2009 | Davison ............ A61M 25/0133 604/500 |
| D601,803 S | 10/2009 | Reishus et al. |
| D609,817 S | 2/2010 | Piller et al. |
| D612,510 S | 3/2010 | Byle |
| 7,674,261 B2 | 3/2010 | Garito et al. |
| 7,749,218 B2 | 7/2010 | Pellegrino et al. |
| 7,763,016 B2 | 7/2010 | Altshuler et al. |
| D625,412 S | 10/2010 | Garito |
| D628,304 S | 11/2010 | Aulwes et al. |
| 7,828,794 B2 | 11/2010 | Sartor |
| 7,875,026 B1 | 1/2011 | Garito |
| 7,879,032 B1 | 2/2011 | Garito et al. |
| 7,879,033 B2 | 2/2011 | Sartor et al. |
| 7,935,110 B1 | 5/2011 | Garito |
| 7,947,037 B1 | 5/2011 | Garito |
| 7,955,327 B2 | 6/2011 | Sartor et al. |
| 7,959,633 B2 | 6/2011 | Sartor et al. |
| 7,975,702 B2 | 7/2011 | Cho et al. |
| 8,002,768 B1 | 8/2011 | Altshuler et al. |
| 8,016,824 B2 | 9/2011 | Buchman, II et al. |
| D646,487 S | 10/2011 | Leppla et al. |
| D652,524 S | 1/2012 | Messner |
| 8,100,898 B2 | 1/2012 | Gregg |
| 8,100,902 B2 | 1/2012 | Sartor |
| 8,113,209 B2 | 2/2012 | Masotti et al. |
| 8,128,622 B2 | 3/2012 | Podhajsky et al. |
| 8,162,937 B2 | 4/2012 | Cunningham et al. |
| D660,448 S | 5/2012 | Lum et al. |
| 8,172,835 B2 | 5/2012 | Leyh et al. |
| 8,190,243 B2 | 5/2012 | Welches et al. |
| 8,231,620 B2 | 7/2012 | Mathonnet |
| 8,235,987 B2 | 8/2012 | Craig |
| 8,251,989 B1 | 8/2012 | Newton et al. |
| 8,317,782 B1 | 11/2012 | Ellman et al. |
| 8,321,031 B1 | 11/2012 | Ellman et al. |
| 8,359,104 B2 | 1/2013 | Epstein |
| D675,829 S | 2/2013 | Jakubow |
| D679,502 S | 4/2013 | Itano et al. |
| 8,449,540 B2 | 5/2013 | Sartor et al. |
| 8,454,591 B2 | 6/2013 | Leyh et al. |
| 8,460,289 B2 | 6/2013 | Sartor |
| 8,506,565 B2 | 8/2013 | DeCarlo |
| 8,540,705 B2 | 9/2013 | Mehta |
| 8,591,509 B2 | 11/2013 | Fry et al. |
| 8,597,292 B2 | 12/2013 | Kerr |
| 8,608,737 B2 | 12/2013 | Mehta |
| 8,632,536 B2 | 1/2014 | Kerr et al. |
| 8,636,733 B2 | 1/2014 | Heard |
| D698,921 S | 2/2014 | Koennecke et al. |
| 8,663,216 B2 | 3/2014 | Davison et al. |
| 8,663,218 B2 | 3/2014 | Heard et al. |
| 8,663,219 B2 | 3/2014 | Heard et al. |
| 8,668,688 B2 | 3/2014 | Rusin |
| D713,150 S | 9/2014 | Maurin et al. |
| 8,845,630 B2 | 9/2014 | Mehta et al. |
| 8,915,948 B2 | 12/2014 | Altshuler et al. |
| 8,945,124 B2 | 2/2015 | Craig |
| 8,961,511 B2 | 2/2015 | Parmer |
| 8,998,891 B2 | 4/2015 | Garito |
| D728,242 S | 5/2015 | Kim et al. |
| D732,164 S | 6/2015 | Woloszko et al. |
| D733,290 S | 6/2015 | Burton et al. |
| D736,462 S | 8/2015 | Hendler et al. |
| 9,132,058 B2 | 9/2015 | Imboden et al. |
| D742,647 S | 11/2015 | Hosier et al. |
| 9,271,785 B2 | 3/2016 | Parmer et al. |
| D757,953 S | 5/2016 | Philips |
| 9,345,531 B2 | 5/2016 | Furnish |
| 9,415,235 B2 | 8/2016 | Galen et al. |
| D767,897 S | 10/2016 | Hosier et al. |
| D773,676 S | 12/2016 | Gufler |
| D793,186 S | 8/2017 | Tinius |
| D805,781 S | 12/2017 | Szymanski et al. |
| D809,139 S | 1/2018 | Marsot et al. |
| D821,759 S | 7/2018 | Szymanski et al. |
| D823,478 S | 7/2018 | Park |
| D830,700 S | 10/2018 | Xue |
| D831,905 S | 10/2018 | Benacquisto et al. |
| D835,845 S | 12/2018 | Graves et al. |
| 10,143,831 B2 | 12/2018 | Juergens et al. |
| D837,395 S | 1/2019 | Gan |
| D839,601 S | 2/2019 | Fang |
| D840,547 S | 2/2019 | Harle et al. |
| D842,491 S | 3/2019 | Fleming et al. |
| D848,677 S | 5/2019 | Thalmann |
| D860,441 S | 9/2019 | Spycher et al. |
| D863,574 S | 10/2019 | Yan et al. |
| D863,580 S | 10/2019 | Lee |
| D864,407 S | 10/2019 | Zhou |
| D870,294 S | 12/2019 | Bechtel et al. |
| D870,304 S | 12/2019 | Du |
| 10,518,097 B2 | 12/2019 | Grez |
| D873,569 S | 1/2020 | Nichols |
| D883,675 S | 5/2020 | Wong et al. |
| D884,203 S | 5/2020 | Segev |
| D892,322 S | 8/2020 | Yang |
| D901,034 S | 11/2020 | Zhang et al. |
| D902,403 S | 11/2020 | Marsot et al. |
| D905,237 S | 12/2020 | Knieriem et al. |
| D905,238 S | 12/2020 | Englert et al. |
| D905,239 S | 12/2020 | Englert et al. |
| D913,483 S | 3/2021 | Boschetti Sacco |
| D919,814 S | 5/2021 | Zikria et al. |
| 2001/0018606 A1 | 8/2001 | Ingle et al. |
| 2002/0029036 A1 | 3/2002 | Goble |
| 2002/0032439 A1 | 3/2002 | Hareyama |
| 2002/0077626 A1 | 6/2002 | Ellman |
| 2002/0115991 A1 | 8/2002 | Edwards |
| 2002/0133149 A1 | 9/2002 | Bessette |
| 2002/0188284 A1 | 12/2002 | To |
| 2003/0009165 A1 | 1/2003 | Edwards |
| 2003/0050634 A1 | 3/2003 | Ellman |
| 2003/0112204 A1 | 6/2003 | Petterson |
| 2003/0130653 A1 | 7/2003 | Sixto, Jr. et al. |
| 2003/0130711 A1 | 7/2003 | Pearson |
| 2003/0139741 A1 | 7/2003 | Goble |
| 2003/0139753 A1 | 7/2003 | Wang |
| 2003/0153906 A1 | 8/2003 | Sharkey et al. |
| 2003/0158545 A1 | 8/2003 | Hovda et al. |
| 2003/0159700 A1 | 8/2003 | Laufer |
| 2003/0163178 A1 | 8/2003 | Davison |
| 2003/0216725 A1 | 11/2003 | Woloszko |
| 2003/0216727 A1 | 11/2003 | Long |
| 2003/0216728 A1 | 11/2003 | Stern et al. |
| 2003/0233037 A1 | 12/2003 | Bencini |
| 2003/0236487 A1 | 12/2003 | Knownlton |
| 2004/0002443 A1 | 1/2004 | Acharya et al. |
| 2004/0002705 A1 | 1/2004 | Knowlton |
| 2004/0006339 A1 | 1/2004 | Underwood |
| 2004/0030329 A1 | 2/2004 | Hagg |
| 2004/0049251 A1 | 3/2004 | Knowlton |
| 2004/0054365 A1 | 3/2004 | Goble |
| 2004/0064175 A1 | 4/2004 | Lessar |
| 2004/0111087 A1 | 6/2004 | Stern |
| 2004/0116979 A1 | 6/2004 | Truckai |
| 2004/0167516 A1 | 8/2004 | Cucin |
| 2004/0181213 A1 | 9/2004 | Gondo |

(56) References Cited

U.S. PATENT DOCUMENTS

| | | |
|---|---|---|
| 2004/0186535 A1 | 9/2004 | Knowlton |
| 2004/0210214 A1 | 10/2004 | Knownlton |
| 2004/0236203 A1 | 11/2004 | Francesco |
| 2005/0004564 A1 | 1/2005 | Wham |
| 2005/0027235 A1 | 2/2005 | Knudsen et al. |
| 2005/0059889 A1 | 3/2005 | Mayer |
| 2005/0090816 A1 | 4/2005 | McClurken |
| 2005/0137662 A1 | 6/2005 | Morris et al. |
| 2005/0154385 A1 | 7/2005 | Heim |
| 2005/0256524 A1 | 11/2005 | Long |
| 2005/0267465 A1 | 12/2005 | Hillier et al. |
| 2006/0009763 A1 | 1/2006 | Goble et al. |
| 2006/0052847 A1 | 3/2006 | Davenport et al. |
| 2006/0173518 A1 | 8/2006 | Kreindel |
| 2006/0009757 A1 | 10/2006 | Long |
| 2006/0259102 A1 | 11/2006 | Slatkine |
| 2007/0005053 A1 | 1/2007 | Dando |
| 2007/0233191 A1 | 2/2007 | Parmer |
| 2007/0055226 A1 | 3/2007 | Garito |
| 2007/0083247 A1 | 4/2007 | Wyeth et al. |
| 2007/0088413 A1 | 4/2007 | Weber et al. |
| 2007/0093804 A1 | 4/2007 | Kaveckis et al. |
| 2007/0093805 A1 | 4/2007 | Auth et al. |
| 2007/0106349 A1 | 5/2007 | Karni |
| 2007/0112342 A1 | 5/2007 | Pearson et al. |
| 2007/0161981 A1 | 7/2007 | Sanders et al. |
| 2007/0213700 A1 | 9/2007 | Davison et al. |
| 2007/0213792 A1 | 9/2007 | Yarosalvsky et al. |
| 2007/0282318 A1 | 12/2007 | Spooner |
| 2008/0004678 A1 | 1/2008 | Kreindel |
| 2008/0009849 A1 | 1/2008 | Goble et al. |
| 2008/0051777 A1* | 2/2008 | Haemmerich ..... A61B 18/1233 606/33 |
| 2008/0058796 A1 | 3/2008 | O'Brien et al. |
| 2008/0091184 A1 | 4/2008 | Knopp et al. |
| 2008/0091185 A1 | 4/2008 | McGill et al. |
| 2008/0119846 A1* | 5/2008 | Rioux ............... A61M 25/0194 606/41 |
| 2008/0125775 A1 | 5/2008 | Morris |
| 2008/0183251 A1 | 7/2008 | Azar et al. |
| 2008/0262490 A1 | 10/2008 | Williams |
| 2008/0312651 A1 | 12/2008 | Pope et al. |
| 2009/0012511 A1 | 1/2009 | Welches et al. |
| 2009/0018531 A1 | 1/2009 | Welches et al. |
| 2009/0024192 A1 | 1/2009 | Mulholland |
| 2009/0036958 A1 | 2/2009 | Metha |
| 2009/0054956 A1 | 2/2009 | Sierra et al. |
| 2009/0062786 A1 | 3/2009 | Garito et al. |
| 2009/0093864 A1 | 4/2009 | Anderson |
| 2009/0112204 A1 | 4/2009 | Aronow |
| 2009/0112205 A1 | 4/2009 | McGill et al. |
| 2009/0138011 A1 | 5/2009 | Epstein |
| 2009/0171341 A1 | 7/2009 | Pope |
| 2009/0248004 A1 | 10/2009 | Altshuler et al. |
| 2009/0248022 A1 | 10/2009 | Falkenstein et al. |
| 2009/0306647 A1 | 12/2009 | Leyh |
| 2009/0306648 A1 | 12/2009 | Podhajsky |
| 2010/0023008 A1 | 1/2010 | Heard |
| 2010/0030107 A1 | 2/2010 | Hancock |
| 2010/0030212 A1 | 2/2010 | Aramayo |
| 2010/0045427 A1 | 2/2010 | Boone, III et al. |
| 2010/0049178 A1 | 2/2010 | Deem |
| 2010/0114088 A1 | 5/2010 | Buchman |
| 2010/0211060 A1 | 8/2010 | Baron et al. |
| 2010/0217254 A1 | 8/2010 | Mehta |
| 2010/0228243 A1 | 9/2010 | Mehta |
| 2010/0228244 A1 | 9/2010 | Hancock |
| 2010/0241116 A1 | 9/2010 | Benamou |
| 2010/0249772 A1 | 9/2010 | Mehta et al. |
| 2010/0262135 A1 | 10/2010 | Berube |
| 2010/0312233 A1 | 12/2010 | Furnish et al. |
| 2011/0046523 A1 | 2/2011 | Altshuler et al. |
| 2011/0087215 A1 | 4/2011 | Aldridge et al. |
| 2011/0087216 A1 | 4/2011 | Aldridge et al. |
| 2011/0144729 A1 | 6/2011 | Weber |
| 2011/0178584 A1 | 7/2011 | Parmer et al. |
| 2011/0218464 A1 | 9/2011 | Iger |
| 2011/0238056 A1* | 9/2011 | Koss ................ A61B 18/1233 606/33 |
| 2011/0276046 A1* | 11/2011 | Heimbecher .......... A61B 34/30 606/35 |
| 2012/0022504 A1 | 1/2012 | Epshtein |
| 2012/0022510 A1 | 1/2012 | Welches et al. |
| 2012/0022512 A1 | 1/2012 | Vaynberg |
| 2012/0095461 A1 | 4/2012 | Herscher |
| 2012/0191072 A1 | 7/2012 | Hancock |
| 2012/0265193 A1 | 10/2012 | Lischinsky et al. |
| 2012/0265196 A1 | 10/2012 | Turner |
| 2013/0006239 A1 | 1/2013 | Pikramenos et al. |
| 2013/0245727 A1 | 9/2013 | Kothare et al. |
| 2013/0245728 A1 | 9/2013 | Galen et al. |
| 2013/0274841 A1* | 10/2013 | Eckhous ................ A61N 1/06 607/101 |
| 2013/0296835 A1 | 11/2013 | Sierra et al. |
| 2014/0025033 A1 | 1/2014 | Mirkov et al. |
| 2014/0182335 A1 | 7/2014 | Lee et al. |
| 2014/0276768 A1 | 9/2014 | Juergens |
| 2015/0005759 A1 | 1/2015 | Welches et al. |
| 2015/0025526 A1 | 1/2015 | Hua et al. |
| 2015/0094914 A1 | 4/2015 | Abreu |
| 2015/0196351 A1 | 7/2015 | Stone et al. |
| 2015/0297908 A1 | 10/2015 | Alinsod et al. |
| 2015/0327926 A1 | 11/2015 | Parmer |
| 2016/0135876 A1 | 5/2016 | Parmer et al. |
| 2016/0256701 A1 | 9/2016 | Furnish et al. |
| 2016/0263387 A1 | 9/2016 | Alinsod et al. |
| 2016/0263388 A1 | 9/2016 | Alinsod et al. |
| 2016/0263389 A1 | 9/2016 | Alinsod et al. |
| 2016/0296278 A1 | 10/2016 | Galen et al. |
| 2017/0071651 A1 | 3/2017 | Allan et al. |
| 2017/0182334 A1 | 6/2017 | Altshuler et al. |
| 2017/0182335 A1 | 6/2017 | Altshuler et al. |
| 2017/0333249 A1 | 11/2017 | Herchman, Jr. et al. |
| 2018/0001103 A9 | 1/2018 | Alinsod et al. |

FOREIGN PATENT DOCUMENTS

| | | |
|---|---|---|
| CN | 101905059 | 12/2010 |
| DE | 2011035 | 10/1970 |
| DE | 3627221 | 2/1988 |
| DE | 9102778 | 5/1991 |
| DE | 4423216 | 8/1995 |
| DE | 19850663 | 3/2001 |
| DE | 10138235 | 1/2003 |
| EP | 0368532 | 5/1990 |
| EP | 0423757 | 4/1991 |
| EP | 0480639 | 4/1992 |
| EP | 0332308 | 9/1998 |
| EP | 1707147 | 10/2006 |
| EP | 2258296 | 12/2010 |
| EP | 2742891 | 6/2014 |
| EP | 2790603 | 10/2014 |
| EP | 2967711 | 1/2016 |
| GB | 2154881 | 9/1985 |
| GB | 2490788 | 11/2012 |
| HK | 20154360005 | 6/2020 |
| JP | S60180394 | 9/1985 |
| JP | S63317073 | 12/1988 |
| JP | H0795985 | 4/1995 |
| JP | H07124101 | 5/1995 |
| JP | H08168495 | 7/1996 |
| JP | 2006-271968 | 10/2006 |
| JP | 2001523513 | 11/2011 |
| JP | 2012254312 | 12/2012 |
| KR | 10-2017-0035486 | 3/2017 |
| WO | 9426228 | 11/1994 |
| WO | 1996022742 | 8/1996 |
| WO | 9634569 | 11/1996 |
| WO | 1996039088 | 12/1996 |
| WO | 1997015238 | 5/1997 |
| WO | 1998016162 | 4/1998 |
| WO | 1998038932 | 9/1998 |
| WO | 1999026546 | 6/1999 |
| WO | 2003103522 | 12/2003 |

(56) References Cited

FOREIGN PATENT DOCUMENTS

| WO | 2004090939 | 10/2004 |
|---|---|---|
| WO | 2008012827 | 1/2008 |
| WO | 2008112931 | 9/2008 |
| WO | 2009031995 | 3/2009 |
| WO | 2009053117 | 4/2009 |
| WO | 2012052986 | 4/2012 |
| WO | 2013090528 | 6/2013 |
| WO | 2014145148 | 9/2014 |

OTHER PUBLICATIONS

Maximum Power Transfer Theorem—Electronics Hub. http://www.electronicshub.org/maximum-power-transfer-theorem/. Accessed Oct. 31, 2019.
Maximum Power Transfer Theorem in DC Theory, http://www.electronics-tutorials.ws/dccircuits/dcp_9.html. Accessed Oct. 31, 2019.
Zelickson, Brian D.,et al., "Histological and Ultrastrcutrual Evaluation of the Effects fo Radiofrequency-Based Nonablative Dermal Remodeling Device," Arch Dermatol, Aug. 14, 2003, pp. 204-209, vol. 140, American Medical Association, United States.
Hantash, Basil M., et al., "Bipolar Fractional Radiofrequency Treatment Induces Neoelastogenesis and Neocollagenesis," Lasers in Surgery and Medicine, Nov. 4, 2008, pp. 1-9, vol. 41, Wiley-Liss, Inc., United States.
Gonzalex-Suarez, Ana, et al., "Thermal and Elastic Response of Subcutaneous Tissue With Different Fibrous Septa Architectures to RF Heating: Numerical Study," Lasers in Surgery and Medicine, Oct. 4, 2014, pp. 183-195, vol. 47, Wiley Periodicals, Inc., United States.
Kist, David, et al., "Ultrastructural Evaluation of Multiple Pass Low Energy Versus Single Pass High Energy Radio-Frequency Treatment," Lasers in Surgery and Medicine, Jan. 5, 2006, pp. 150-154, vol. 38, Wiley-Liss, Inc., United States.
"The Effect of Heat on Collagen and Neocollagenesis," Ultherapy.com, Jul. 20, 2011, 78 pages, available from http://www.ultherapy.com/uploads/document/professional/Effects-of-Temperature-on-Collagen.pdf. (last accessed May 9, 2018).
Abraham, Manoj T., et al. "Monopolar Radiofrequency Skin Tightening," Facial Plastic Surgery Clinics of North America, 2007, pp. 169-177, vol. 15, Elsevier Inc.
Sadick, Neil, "Tissue Tightening Technologies: Fact or Fiction," Aesthetic Surgery Journal, Dec. 11, 2007, pp. 180-188, vol. 28 No. 2, Sage Publications, United States.
Lauback, Hans J., et al., "Intense Focused Ultrasound: Evaluation of a New Treatment Modality for Precise Microcoagulation within the Skin," American Society for Dermatologic Surgery, Inc., May 2008, pp. 727-734, vol. 34, Blackwell Publishing, United States.
White, W. Matthew, et al., "Selective Transcutaneous Delivery of Energy to Porcine Soft Tissues Using Intense Ultrasound (IUS)," Lasers in Surgery and Medicine, Dec. 27, 2007, pp. 67-75, vol. 40, Wiley-Liss, Inc., United States.
Hayashi, Kei, et al., "The Effect of Thermal Heating on the Length and Histologic Properties of the Glenohumeral Joint Capsule," The American Journal of Sports Medicine, 1997, pp. 107-112, vol. 25 No. 1, Sage Publications, United States.
Vangsness Jr., C. Thomas, et al., "Collagen Shortening: An Experimental Approach with Heat," Clinical Orthopedics and Related Research, Mar. 24, 1995, pp. 267-271, vol. 337, Lippincott-Raven Publishers.
Lin, Sung-Jan, et al., "Monitoring the Thermally Induced Structural Transitions of Collagen by Use of Second-Harmonic Generation Microscopy," Optics Letters, Mar. 15, 2005, pp. 622-624, vol. 30 No. 6, Optical Society of America.
Paul, Malcolm, et al., "Three-Dimensional Radiofrequency Tissue Tightening: A Proposed Mechanism and Applications for Body Contouring," Aesth Platic Surgery, Jul. 6, 2010, pp. 87-95, vol. 35., Springer.
Hayashi, Kei, et al., "Effect of Nonablative Laser Energy on the Joint Capsule: An in Vivo Rabbit Study Using a Holmium:YAG Laser," Lasers in Surgery and Medicine, Feb. 21, 1996, pp. 164-171, vol. 20, Wiley-Liss, Inc., United States.
Invitation to Pay Additional Fees for PCT Application No. PCT/US2017/040585, dated Oct. 13, 2017, 23 pages.
International Search Report and Written Opinion for PCT Application No. PCT/US2017/040585, dated Dec. 6, 2017, 24 pages.
Third Party Submission in PCT Application No. PCT/US2017/040585, filed Jan. 29, 2018, 30 pages.
Third Party Submission in U.S. Appl. No. 15/640,710, filed Feb. 7, 2018, 58 pages.
International Search Report and Written Opinion of the International Searching Authority in PCT/US14/29862 dated Oct. 23, 2014.
Non-Final Office Action for U.S. Appl. No. 14/205,021, dated Jul. 28, 2016.
Office Action in Canadian Application No. 3,089,137, dated Aug. 11, 2021, 3 pages.
Fritzpatrick, et al. (2003). 'Multicenter study of noninvasive radiofrequency for periorbital tissue tightening'. Lasers in Surgery and Medicine 2003; 33:232-242. (11 page total).
Fritz, et al. (2004). 'Radiofrequency treatment for middle and lower face laxity'. Arch Facial Plastic Surgery 2004; 6:370-373. (4 pages total).
Kushikata, et al., (2005). 'Is topical anesthesia useful in noninvasive skin tightening using radiofrequency?' J. Dermatologic Surgery 2005; 31:526-533. (8 page total).
Brunelle et al, A Bipolar Electrode for Vascular Electrocoagulation with Alternating Current. Radiology, vol. 137, No. 1, pp. 239 240, Oct. 1980.
Extended European Search Report dated Nov. 4, 2016 in European Application No. 14762910.9.
Non-Final Office Action for U.S. Appl. No. 14/214,627, dated Aug. 19, 2016, 16 pages.
Final Office Action for U.S. Appl. No. 14/214,627, dated Mar. 8, 2017, 21 pages.
Non-Final Office Action for U.S. Appl. No. 14/214,627, dated Jul. 14, 2017, 22 pages.
Final Office Action for U.S. Appl. No. 14/214,627, dated Oct. 31, 2018, 26 pages.
Non-Final Office Action for U.S. Appl. No. 14/214,627, dated May 25, 2018, 23 pages.
Final Office Action for U.S. Appl. No. 14/214,627, dated Sep. 21, 2018, 24 pages.
Non-Final Office Action for U.S. Appl. No. 14/214,627, dated Apr. 10, 2019, 19 pages.
Non-Final Office Action in U.S. Appl. No. 16/269,314, dated Feb. 14, 2022, 28 pages.
Restriction Requirement in U.S. Appl. No. 16/269,314, dated Jul. 29, 2021, 8 pages.
Third Examination Report in Australian Application No. 2019217623, dated Sep. 21, 2021, 4 pages.
Extended European Search Report in European Application No. 19750304, dated Oct. 21, 2021, 6 pages.
Chinese-language Office Action (with English-language translation provided) dated Jul. 12, 2012, issued by China's State Intellectual Property Office in Chinese Application No. 201010201340.2, 4 pages.
European Search Report for European Application No. 10164893, dated Oct. 11, 2010, 6 pages.
European Search Report dated Jan. 23, 2009 for European Patent application No. 08252879.5; 9 pages.
Office Action for Japanese Application No. 2008-218931, dated Feb. 5, 2013, 4 pages.
Notice of Reasons for Refusal for Japanese Application No. 2008-218931, dated Aug. 5, 2013, 6 pages.
European Search Report for European Application No. 10176756.4, dated Dec. 28, 2010, 5 pages.
European Search Report for European Application No. 99303449, dated Oct. 6, 1999, 3 pages.
International Search Report and Written Opinion in PCT Application No. PCT/US2019/016883, dated Jun. 24, 2019, 12 pages.
Extended European Search Report dated Nov. 8, 2016 in European Patent Application No. 14768330.4.

(56) References Cited

OTHER PUBLICATIONS

International Search Report and Written Opinion for PCT Application No. PCT/US2014/029862, dated Oct. 23, 2014.
Examination Report in Australian Application No. 2019217623, dated Oct. 27, 2020, 5 pages.
Restriction Requirement for U.S. Appl. No. 29/698,791, dated Mar. 29, 2022, 11 pages.
Office Action in Korean Application No. 10-2020-7025344, dated Mar. 29, 2022, 10 pages.

\* cited by examiner

SURGICAL INSTRUMENTS AND SYSTEMS WITH MULTIMODES OF TREATMENTS AND ELECTROSURGICAL OPERATION

RELATED APPLICATIONS

This application claims the benefit of and priority to U.S. patent application Ser. No. 14/214,627, filed on Mar. 14, 2014, which claims the benefit of and priority to U.S. Provisional Application Ser. No. 61/794,732, filed Mar. 15, 2013, the contents of which are hereby incorporated by reference as if recited in full herein for all purposes.

BACKGROUND

In general the inventive subject matter is directed to a multimode surgical instrument that provides for (1) multiple modes of electrosurgical operation, and/or (2) multiple modes of surgical treatment. In certain embodiments, the inventive subject matter is directed to a multimode electrosurgical system with a set of return electrodes that can be variably engaged into operation to control a temperature at select electrodes in the set or at a target area adjacent the electrodes. The inventive subject matter, while adaptable to many surgical and therapeutic applications, is particularly suited for use in a system for liposuction. Accordingly, hereafter, a liposuction application will generally be used to illustrate the principles of the inventive subject matter and various possible embodiments thereunder.

In general, a liposuction procedure involves the insertion of a cannula into an area of a patient's body where subcutaneous fat tissue 1 is present. The cannula includes a valve assembly that couples to a suction source. The operator applies suction to the cannula or other hollow shaft to remove fatty tissue that is disrupted by a disrupter associated with the cannula. The disrupter may be a mechanical element, such as blade, or an energy emitter for disruption by targeted energy. For example, the tip of a cannula can be configured to scrape fat tissue. In other known systems, the cannula supports a laser device or ultrasonic device for targeting disruptive energy into tissue to fragment, melt, or vaporize tissue. One disadvantage of typical laser-liposuction devices is that the laser fiber is in placed in the main channel or lumen of the cannula so there cannot be simultaneous melting of fat by the laser and suction of the disrupted fatty materials.

Liposuction procedures may be dry field, wet field, or semi-wet field procedures. In a dry field, the cannula is inserted into the target area without the introduction of any fluid. In a wet field, a fluid is introduced into the target area through a lumen in the instrument. The introduced fluid may serve various functions. For example, it can be an irrigant that facilitates the suctioning of disrupted tissue. A semi-dry field is one where the target area is lightly irrigated. Accordingly, in a liposuction procedure the suctioned material may be primarily fatty material or a mixture of fatty material and an introduced fluid.

A significant disadvantage of all liposuction procedures is that when subcutaneous fat is removed from below the dermis, skin tension is reduced causing unsightly wrinkling, sagging or other surface irregularities in the skin. The degree of such irregularities may necessitate a surgeon to excise skin tissue and suture the exposed edges to tighten the skin surface. This is highly undesirably on several fronts, including the creation of scars and additional surgical risk.

Accordingly, there is a need for improved surgical and therapeutic instruments that simultaneously address multiple surgical and therapeutic needs. In the case of liposuction, there is a need for systems and instruments that not only meet the requirements for disruption and removal of fatty tissue, but also mitigate the cosmetic impact of liposuction on the skin's appearance.

SUMMARY

In some embodiments, the inventive subject matter is directed to a multimode electrosurgical system having an electrosurgical instrument with a first electrode configuration that operates in a bipolar mode and second electrode configuration that operates in a monopolar mode. In other embodiments, the inventive subject matter is directed to an instrument and system that provide multiple modes of surgical and/or therapeutic treatments, at least one being an electrosurgical mode of treatment, the instrument including at least one active electrode on a working portion, and the working portion including or supporting at least one non-electrosurgical functional element, the instrument including at least one operational return electrode configuration of selectively variable surface area.

The foregoing is not intended to be an exhaustive list of embodiments and features of the inventive subject matter. Persons skilled in the art are capable of appreciating other embodiments and features from the following detailed description in conjunction with the drawings. The following is a description of various inventive lines under the inventive subject matter. The appended claims, as originally filed in the underlying provisional application, and/or in this document, or as subsequently amended, are hereby incorporated into this summary section as if written directly in.

BRIEF DESCRIPTION OF THE DRAWINGS

The following figures show embodiments according to the inventive subject matter, unless noted as showing prior art. The Figures are not intended to be of scale.

DETAILED DESCRIPTION

Figure 1:
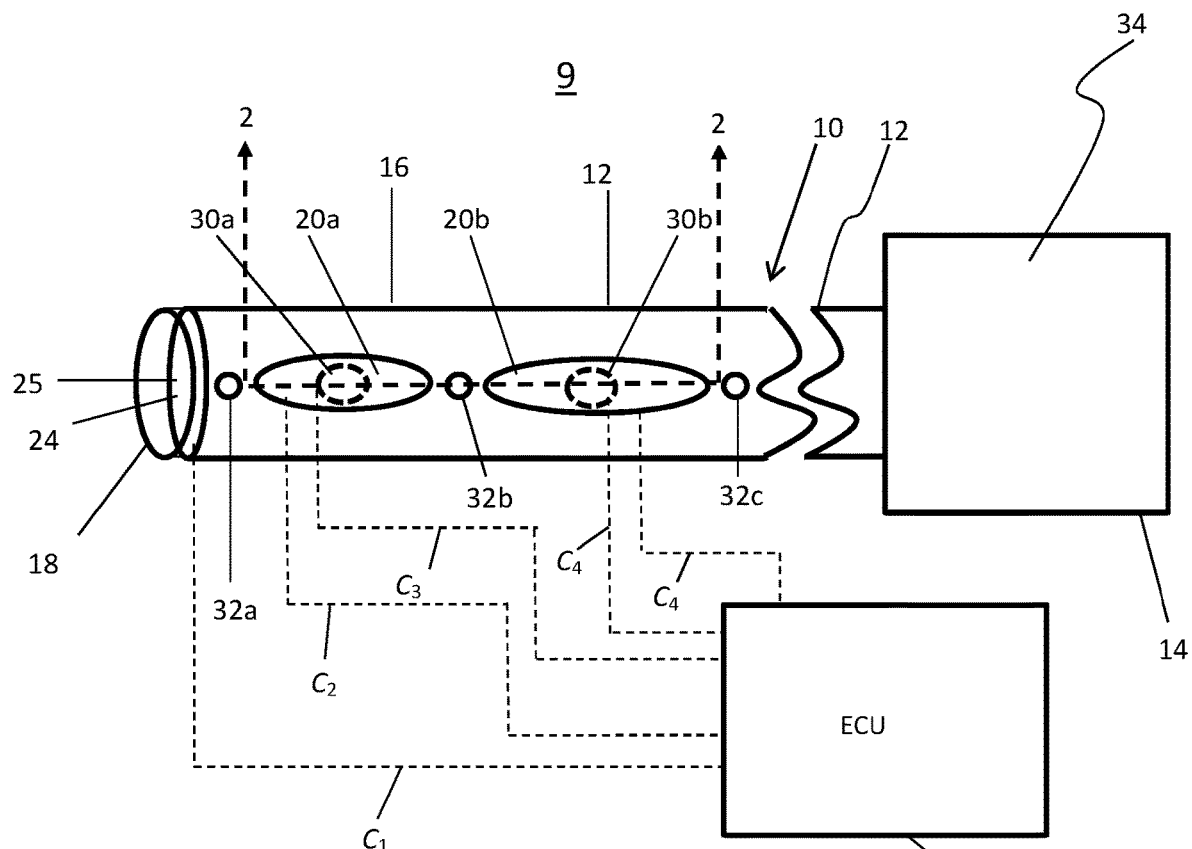
FIG. 1 shows a schematic plan view of a system with a medical instrument with a working portion, which may have variable length, as indicted by broken lines.

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

Multiple Modes of Electrosurgical Operation

In some embodiments, the inventive subject matter is directed to a hybrid electrosurgical system and related instruments with a first electrode configuration that operates in a bipolar mode and second electrode configuration that operates in a monopolar mode. In certain embodiments, the inventive subject matter is directed to a multimode electrosurgical system with a set of return electrodes that can be variably engaged into operation to control a temperature at select electrodes in the set or at adjacent or nearby tissue.

In one possible embodiment, the instrument includes an active electrode, i.e., an electrode that is energizable and configured to deliver radio frequency ("RF") energy to a target area in or on a patient's body. For example, the active electrode may be configured for vaporization, cutting, coagulating, ablating, or fulgurating of target tissue using parameters that are well known in the art. Electrode configurations for specific effects are known to persons skilled in the art. For example, electrodes with low surface area points of contact will be more suited for cutting of tissue, while broader surface areas are more suited for coagulating of tissue. The desired effect is also dependent on the frequency, power, waveform, and duty cycles of RF energy input though the electrode. The parameters for a desired effect are generally known to persons skilled in the art. In general, RF energy is supplied to the instrument by an electrosurgical generator that outputs a power profile to one or more active electrodes on an instrument. There are many commercially available sources of such generators, which are also known as Electrosurgical Control Units ("ECUs"). As used herein, ECU means the generator and associated control circuits. Control circuits need not be in the same housing as generator components and some may even reside remotely under separate housings or on the surgical instrument that couples to the generator components.

In addition to one or more active electrodes, electrosurgical instruments include at least one return electrode, and a current path is defined between the active and return electrode. In the case of a bipolar instrument, one or more return electrodes are disposed on the body of the instrument. The return electrode or electrodes provide a return path to the generator. In a monopolar instrument, the return electrode is not on the instrument but is remotely placed against a portion of the patient's body, typically against the buttocks. Such return electrodes may be referred to in the art as "patient pads." They have sufficiently broad surface area so that current density is safely reduced to avoid burning the patient. One advantage of the inventive subject matter is that it provides multiple electrode configurations that allow for varying modalities of polarity: strictly bipolar operation, strictly monopolar operation, or alternating between bipolar and monopolar operation. As discussed in more detail below, the instrument shown in the Figures is configured for such varying modes of electrosurgical treatment.

Multiple Modes of Surgical Treatment

In some embodiments, the inventive subject matter generally relates to surgical and therapeutic systems and related instruments that provide multiple modes of treatments, at least one being an electrosurgical treatment. For example, the Figures show an instrument with the following modes: a first mode is used to perform liposuction on a patient; and a second mode is used to perform skin tightening in the same area as the liposuction. The second mode may be performed concurrently or separately from the liposuction mode.

Figure 2:
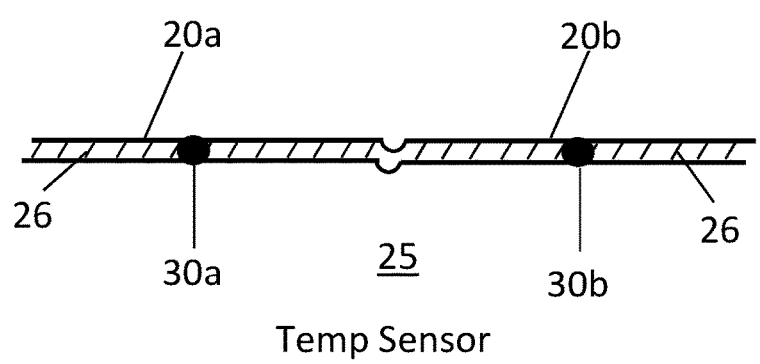
FIG. 2 is a schematic, side-elevational view of a cross section of the instrument of FIG. 1, taken along line 2-2 in FIG. 1.

FIG. 1 shows a system 9 that includes an instrument 10 and an associated electrosurgical control unit ("ECU") 11 that supports electrosurgical modes of operation for the instrument. In the embodiment shown, the electrosurgical instrument 10 includes a working portion 12 that extends distally from a handle or handpiece 14, which may have controls for the user to activate or deactivate functions for the instrument. FIG. 2 shows a cross-section of the distal tip portion of the instrument taken along line 2-2 in FIG. 1. The working portion is typically elongate and is intended for use in or over a target area of a patient's body. The handle may also serve as a housing for components, e.g., for circuitry. In other instances, a graspable handle 14 is spaced from the housing of circuits. The distal end portion 16 of the working portion includes one or more electrodes, such as electrodes 18, 20a, 20b and/or 28. The system includes circuits or communication channels, e.g., $C_1$-$C_4$, for activity and controlling electrodes and other components on the instrument.

The ECU is configured to provide power to the instrument for energizing one or more active electrodes that may be disposed on the instrument. As described more fully below, the ECU can be configured to provide energy having a selected radio frequency and waveform.

Typically, a cable (not shown) extends between an electrical connector on the ECU control and an electrical connector on the electrosurgical instrument to electrically couple one or more conductive elements on or within the instrument to one or more corresponding conductive elements of the controller.

Figure 3A:
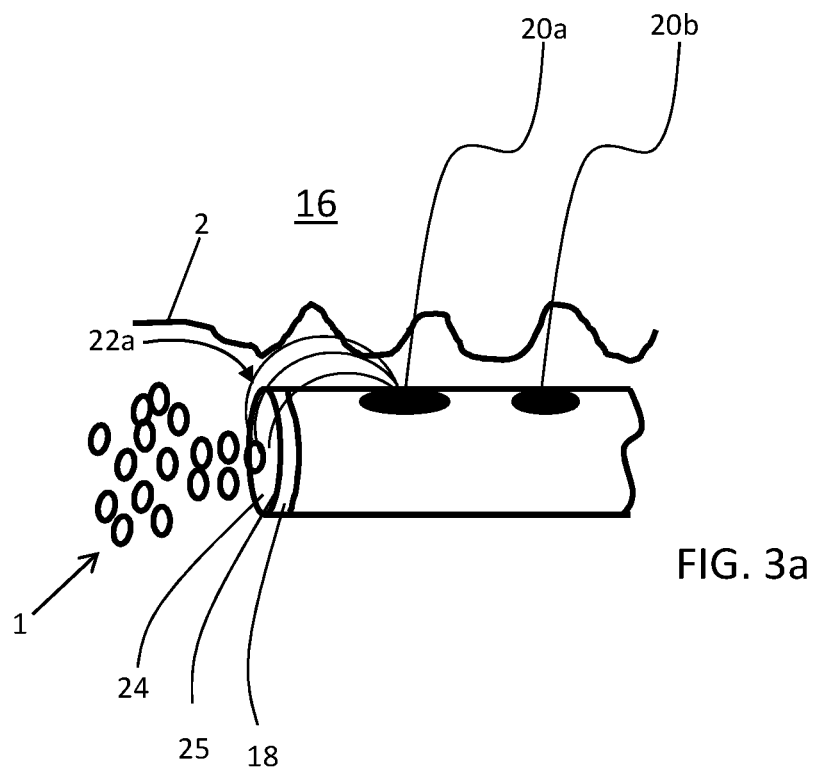
FIG. 3A is a schematic view of a first mode of operation of the instrument of FIG. 1 in a target area of a patient's body.
Figure 3B:
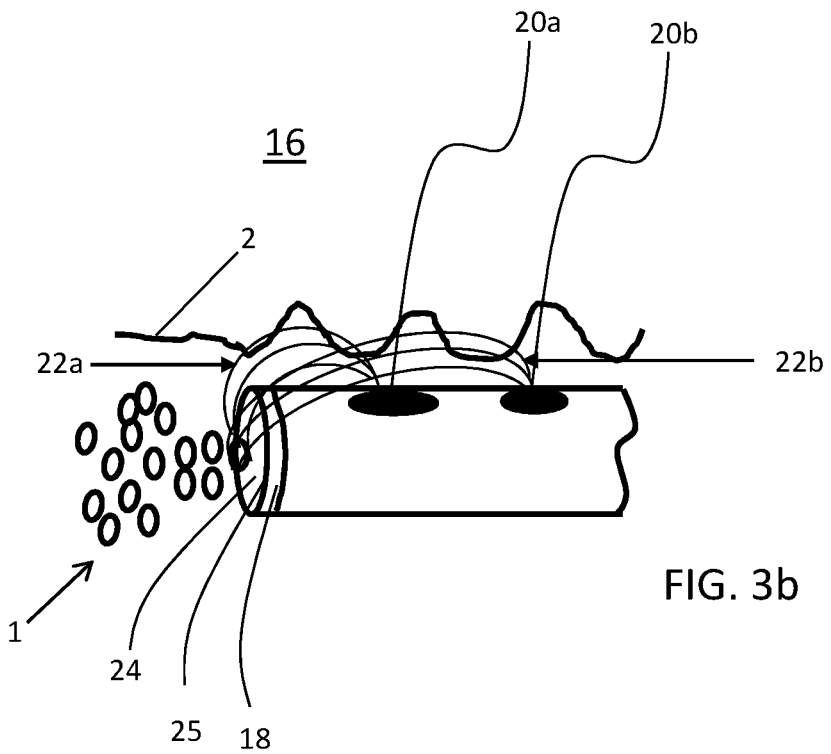
FIG. 3b is a schematic view of a second mode of operation of the instrument of FIG. 3A in the target area of the patient's body.

In certain embodiments, the inventive subject matter overcomes the disadvantages in the field of liposuction by providing for simultaneous disruption of fatty tissues and skin tightening in the target area of a patient. Heat induces collagen denaturation and collagen contraction, which in turn leads to new collagen formation in the dermis, which also results in epidermal tightening. While not intending to be bound by any theory of operation, under the inventive subject matter skin tightening is believed to be accomplished in the following manner. One or more return electrodes (e.g., 20a, 20b) of appropriate dimensions and shape are oriented toward the undersurface of the dermis where fatty tissue is being removed. (FIGS. 1-3b.) The return electrodes are conductive elements that conclude a current path (e.g., 22a, 22b) with the active electrode (e.g., 18). Heat is generated along the path, as resistive heating from the current. (FIGS. 3a-3b.) Accordingly, non-ablative, thermal energy emanates from a current path. The heat transfers to the tissue adjacent the current path and/or the return electrodes.

In the example of the Figures, the active electrode 18 is configured as a ring disposed about the distal opening 24 of working portion 12, which in this case is a cannula with one of more lumens 25. The inventive subject matter is not limited to ring-shaped active electrodes. Any other shape that achieves a desired effect can be used. For example, the active electrode at the distal end of the instrument 10 could have a bull-nose like configuration.

Looking at instrument 10, a pair of return electrodes is disposed in line with the longitudinal axis of the cannula, and on the outer surface of the cannula. The instrument or associated ECU is configured with circuitry to allow for manual or automatic switching on and off of the return electrodes according to predefined parameters such as temperature or duty cycles. The ECU also includes similar manual or automatic switching circuitry for switching on and off a patient pad coupled to the system.

The cannula has side walls defining at least one lumen (e.g., 25) for transporting materials or things from or to the target area of a patient. The cannula shown in the Figures has a circular cross-section, but the cross-section can vary. For example, it can be an oval, square, hexagonal, a complex curve, or any other shape that defines a lumen or serves an intended purpose. The working portion may also have multiple lumens of desired cross-sections that run in parallel fashion along the working portion. For example, a first lumen could be connected to a suction source for applying suction at a target site and removing loose materials. That same lumen could optionally be used for other purposes. For example, it could serve as the lumen for introduction of a fluid to the target site. A second lumen could be used to introduce another instrument or tool, such as a laser fiber, that delivers energy to the target site or to introduce a fluid or other material to the target site. A second or third lumen could be used to provide a channel for introducing an endoscope for viewing a target area. The distal end portion 16 of the instrument could also include a built-in image sensor for imaging at a target site, and optionally a light source, both of which are well-known features in the field of endoscopy and minimally invasive surgery.

Although the working portion for instrument 10 shown in the Figures has a straight shaft, the inventive subject matter is not limited to that configuration. For example, the distal portion 16 of the shaft could be angled off of a proximal, straight portion, i.e., a jog off the major longitudinal axis of the instrument. Such angling could allow the return electrodes to make better contact with tissue when the targeted tissue 1 is parallel to the shaft. Alternatively, the return electrodes could be placed on the angled portion when the targeted tissue is transverse to the major, longitudinal axis of the working portion.

In some embodiments suitable for skin tightening, particularly skin tightening in connection with a liposuction procedure, a cannula of about 4 mm outer diameter is suitable. The return electrode configuration on such a cannula may be about 7 mm wide and about 23 mm long (or other dimensions of similar surface area), as a single return electrode unit or aggregation of smaller return electrode units (e.g., return electrodes 20a and 20b). The return electrodes may be made of a suitable conductive material such as aluminum, copper, silver, or alloys of conductive materials. The return electrodes may be disposed on the cannula as a thin foil or sheet of conductive material. They could also be formed as a coating on the surface of the cannula by other means. For example, a vapor deposition or metal printing technique could be used to metallize an area of a cannula. Because cannulas and other working portion configurations are typically made of a conductive material, e.g., stainless steel, a non-conductive layer 26 of material will be disposed between the main body (or other conductive substrate) of the cannula and the return electrodes. The return electrodes may have varying shape and surface area, but for use in skin tightening they would at least be configured for a non-ablative, thermal effect on tissue.

In operation, a current path is defined by (1) one or more active electrodes (e.g., 18), which are used to disrupt fatty tissue, disposed at the distal end portion 16 of the cannula 12; and (2) one or more operational return electrode or electrodes (e.g., 20a and 20b) that are spaced from the active electrode(s) and disposed on the outer surface of the cannula. The current flow occurs along the defined path(s) 22a and/or 22b when the instrument is operated in bipolar mode. A remote electrosurgical generator supplies the power to drive the current. As the instrument is steadily used in a procedure, the area of the current path leading to the operational return electrodes will heat. To control temperature so that that the dermis 2, which is the layer directly above subcutaneous fat, will heat within selected temperature range, each active electrode may be placed in a switchable circuit with a monopolar operating mode of the generator and one or more patient pads 28 on the exterior surface of the patient's body.

To effect skin tightening, the dermis is maintained between a target temperature range of from 39 degrees or thereabout C to 55 degrees C. or thereabout, with a temperature of 42 degree or thereabout being suitable. Tissue temperature may be monitored directly or by approximation by monitoring temperatures at the return electrode adjacent the treated tissue.

Figure 4:
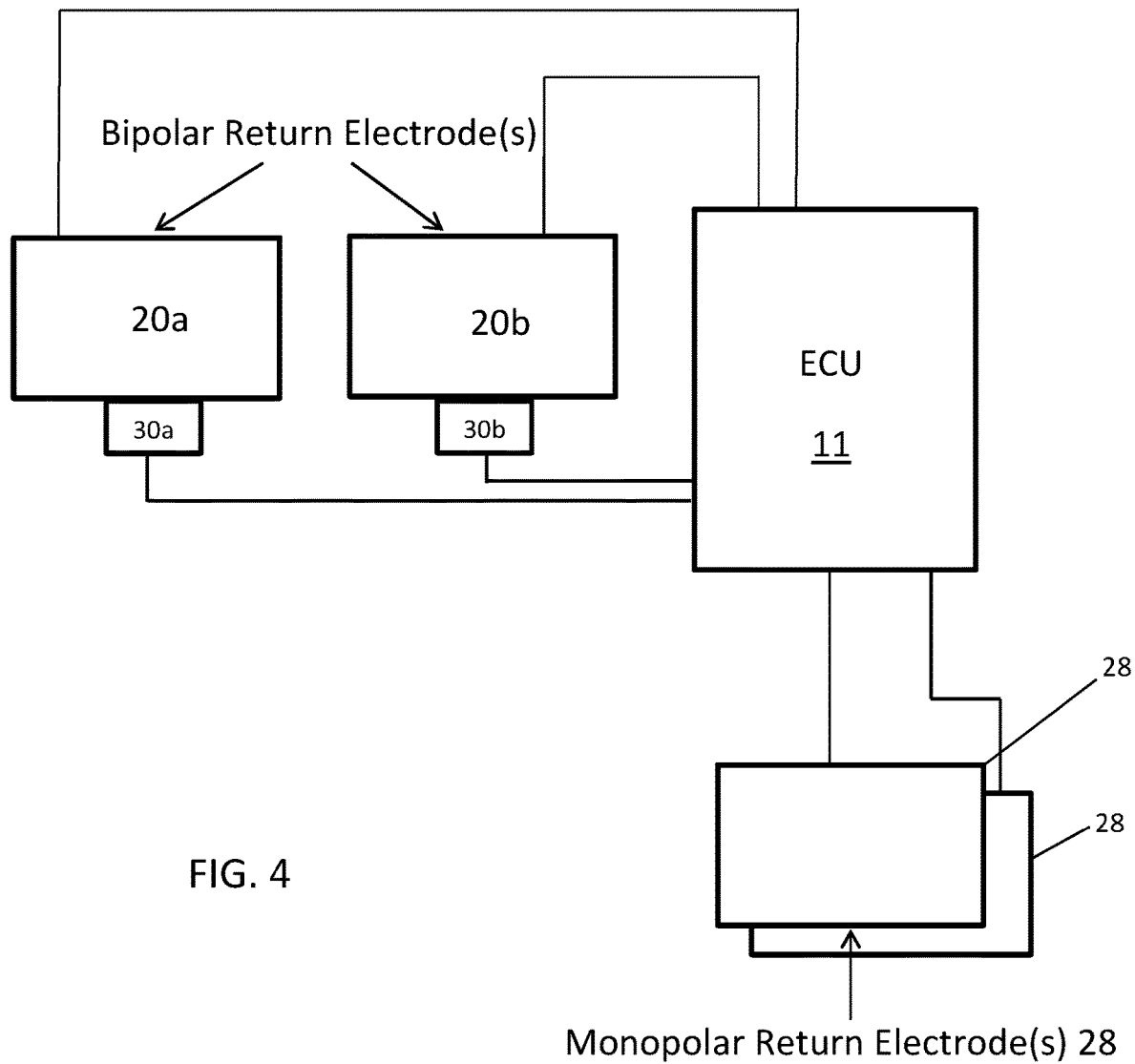
FIG. 4 is a block diagram of a set of components and associated channels for the components to intercouple with an ECU for purposes electrically activating or deactivating the components or communicating data signals.

Referring to FIG. 4, the system may be configured with upper and lower limits for switching the return electrodes from bipolar mode to monopolar mode. In bipolar mode, the functioning return electrodes are the onboard return electrodes (e.g., 20a and/or 20b) on the surface of the cannula. But in monopolar mode, the onboard return electrodes are deactivated from being in circuit with the generator and at least one patient pad 28 in contact with a patient is activated into a circuit in communication with the generator. Relative to the return electrodes on the cannula, the broader surface area of the patient pad provides substantially reduced current density and consequently relatively little heating. While in the monopolar operational mode, the target tissue 1 adjacent the return electrodes 20a, 20b on the cannula can cool back into the defined temperature range for skin tightening. In some embodiments, the patient pad may be maintained on the outside of the epidermis at the area of dermis being treated, or thereabout, thereby providing a more direct and efficient current path.

The inventive subject matter contemplates the use of a single patient pad 28 or multiple, spaced-apart patient pads, as seen in FIG. 4. Typically a monopolar patient pad is an electrode of about 4 inches by 5 inches (or different dimensions or shapes but similar surface area). If multiple pads are used, they can be selectively activated and deactivated. For example, if a first pad is heating beyond predefined limits, a second pad could be activated, with or without deactivating the first pad.

In certain embodiments, the inventive subject matter contemplates a system with one or more return pads 28. In general, the ratio of the area of the return pad relative to the area of the active portion (active end-effector) determines the relative proportion of energy that is deposited at each location. The larger the ratio, the greater the percentage of heat generated in the tissue at the smaller terminus. To control the amount of heat generated in the dermal layer, while at the same time assuring that there is sufficient heat to melt or otherwise disrupt the fat at the end effector, the system switches between the various return pads.

One possibility envisioned is for the return pad to be coupled to the hand of the physician operating instrument 10. During the course of the lipo-suction procedure, it is not unusual for the physician to apply external pressure to the patient over the area being evacuated. By having one return pad coupled to the physician's hand (palm and/or fingers), the return pad is thus always maintained in an ideal location relative to the treatment area. Accordingly, the inventive subject matter contemplates systems and methods related to the coupling of a return pad on the user's hand. A return pad could, for example, be in glove form or have finger straps or bands to enable the pad to secure to the user's hand or fingers.

In other embodiments, the inventive subject matter contemplates components and methods for control over impedance during a procedure. For example, one possibility with having the return electrode disposed on either the shaft of the liposuction probe or to the hand of the physician is that contact between the patient and the return electrode can be intermittent. Intermittent contact results in a loss of energy flow to the active electrode and may also generate unwanted sparking at the return electrode. A solution to this is to have at least one return electrode designated for constant service during a procedure and one or more other return electrodes, such as those on the cannula or coupled to a user's hand, that can have varying degrees of contact, from no contact to full contact with treatment areas. The return electrode designated for constant service can control the flow of energy between the various pads so as to (1) maintain both a constant flow of energy and (2) help reduce or eliminate unwanted sparking or deactivation of the active electrode.

The parameters for design and operation of skin tightening systems are found in various patents under a common assignment to the assignee of this application. These include U.S. Pat. Nos. 8,359,104, 8,321,031, and 8,317,782, the contents of which are incorporated herein by reference in their entireties. However, these devices are configured with an active electrode for direct application of RF energy to the epidermal side of the skin. In contrast, the embodiments contemplated herein use the heat generated off the current path to the return electrode, not the active electrode, to apply thermal energy to the dermis to heat it to skin-tightening temperatures. The active electrode is in a cutting mode to disrupt target tissue and is in a surgical mode of electrosurgical treatment; it is not in an aesthetic mode of electrosurgical treatment (see discussion below). Nonetheless, in some possible embodiments, a liposuction instrument could be configured with an active electrode for application of RF energy to the dermis using an aesthetic or similar therapeutic, non-surgical mode of treatment.

To measure or estimate temperature at selected target tissue and/or on instrument components, temperature sensors (e.g., 30a, 30b) may be optionally incorporated into the instrument 10, as seen in FIGS. 1-2, for example. For example, one or more thermistors may be incorporated into the instrument. As seen in the Figures, separately readable thermistors 30a, 30b are disposed adjacent to each return electrode 20a, 20b to measure the temperature in the proximity of the electrodes that results from heat transfer. In this example, the thermistors are integrated between the lower surface of the return electrodes 20a, 20b and the top surface of the layer 26 of insulating material on which the return electrodes are disposed. An infrared sensor may also be disposed on or off instrument 10 and associated with the return electrodes or otherwise to monitor temperature at the target site.

FIGS. 3A and 3B illustrate a distal working portion 16 of a cannula 12 with two return electrodes 20a, 20b. The distal portion 16 is at a subcutaneous layer of fatty tissue 1, which is the target for liposuction. In a first mode of operation (FIG. 3A), where at t (time)=1, only a first return electrode 20a is in operation and working within a temperature range for skin tightening. The globular area represents fatty tissue in front of the distal tip portion 16 of the instrument. An active electrode 18 at the tip is energized and disrupting that tissue. Above and parallel to the distal working portion is the underside of the dermis 2. The current path 22a is indicated by the arcing lines run from the distal tip to a first, distal return electrode 20a. This represents a current path from the active electrode 18 to the first return electrode 20a. A second, proximal return electrode 20b is deactivated and not in the current path at t=1. In a second mode of operation (FIG. 3B), where t=2, a temperature that exceeds a defined limit has been sensed for the targeted dermis. When this occurs, the second return electrode 20b is activated into operation. This is indicated by a second set of arcing lines for a current path 22b, which extends beyond the first current path 22a all the way to the second return electrode 20b. With the second return electrode 20b activated into operation along with the first electrode 20a, the aggregate surface area of return electrodes has increased and the overall temperature of the area by the return electrodes can be maintained under the defined limit for a given power profile.

Modulation of tissue temperature can be achieved by alternating between different return electrodes in a set of return electrodes included in a system, e.g., the electrodes disposed on a working portion of an instrument and/or a patient pad. Each return electrode may be separately addressable and switchable. This allows for parallel or sequential use of the return electrodes. It also allows for variable overall current densities based on the aggregate surface area of the return electrodes in service. For example, if a first return electrode is too hot, a second one can be activated into service to increase the aggregate surface area and thereby decrease overall heating. Similarly, by providing an array of two or more return electrodes on the surface of the cannula, some return electrodes may always be kept in service to heat tissue for skin tightening while others are in a cooling phase.

In the case of a liposuction instrument with return electrodes for skin tightening, temperature readings could be taken at the underside of the dermis or at the epidermis, or at both locations to monitor for temperatures sufficient to denature collagen and to help avoid overheating of the epidermis or other tissue. Accordingly, the inventive subject matter is directed to systems and methods for controlling the temperature of tissue in contact with a defined set of return electrodes by varying the aggregate surface area of all return electrodes (whether in a bipolar or monopolar circuit) that are in a current path with an active electrode.

As can be seen in the Figures, the instrument 10 optionally may include one or more apertures (e.g., 32a, 32b, 32c) about the return electrodes 20a, 20b that are in communication with channels (e.g., 17) in the instrument that can couple with a suction source (not shown). The application of suction will cause the instrument to draw up against adjacent tissue to bring the return electrode in contact or closer contact with the tissue that is targeted for heating and tightening. In the embodiment of FIG. 1, the apertures 32a, 32b, 32c are in line with the return electrodes 20a, 20b. In addition to, or instead of, such an arrangement, the apertures could be spaced along one or both sides of the electrodes in a generally parallel fashion.

Figure 5:
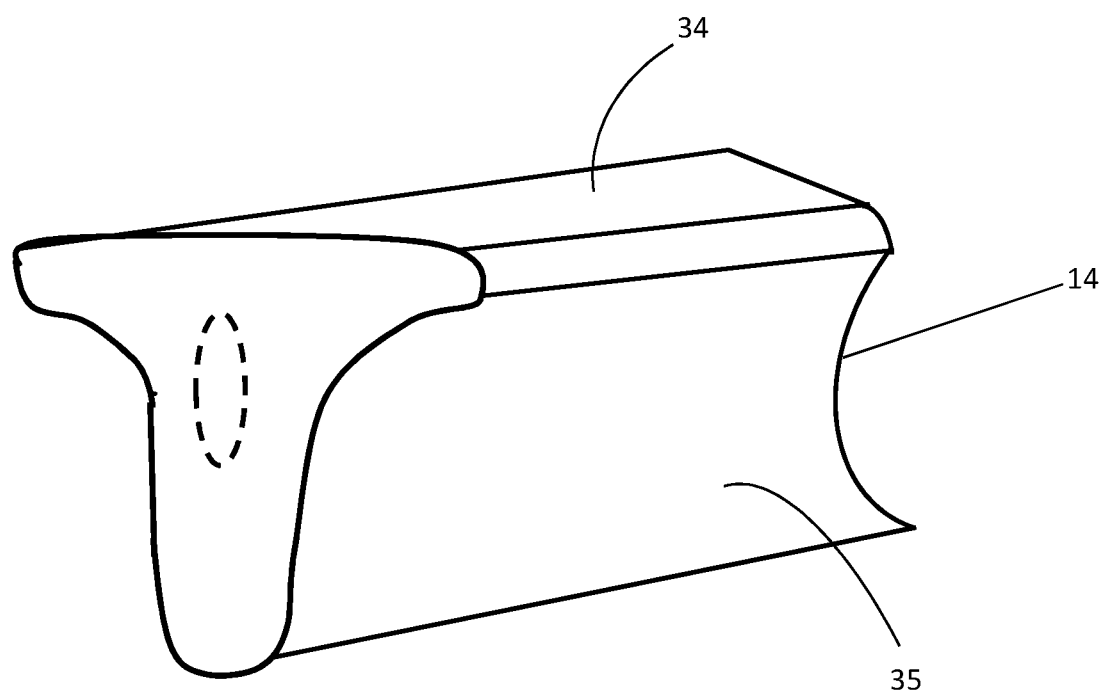
FIG. 5 is a schematic, front-perspective view of one possible form for handle or hand piece used on the instrument of FIG. 1, with the handle or hand piece being shown in isolation from the working portion of the instrument.

In some embodiments, the instrument is configured for establishing orientation with target tissue so that return electrodes may be positioned adjacent to target tissue. For example, the side 34 of the shaft or handle 14 in line with the return electrodes 20a, 20b could have a different shape or dimension than other sides. For example, cannula 12 is connected to a handle 14 having a generally triangular cross section (FIGS. 1 and 5). One side 34 of the handle, which corresponds to the side on the cannula where the return electrodes are disposed, has a relatively broad, planar surface. The other two surfaces 35 are not planar but arcuate. In addition to geometrical configurations that differentiate a return-electrode side or other defined side from other sides, other ways of determining orientation are contemplated. For example, orientation could be determined using an imaging sensor that allows for viewing from the return electrode side of the instrument or inertial sensors that follow motion. Another approach is color coding or placing of any other graphical indicator (e.g., letters, words, numbers, symbols) or other visible indicator (e.g., light emitters) on a side of the handle or working portion that marks that side as corresponding to a predefined area on the instrument. This approach is not limited to use with return electrodes but also can be used to indicate the orientation of other functional features in the instrument. If there are multiple placements of return electrodes or other features spaced about the circumference, the handle or other portion of the instrument that extends from a target can be coded with corresponding indicia of orientation.

Figure 6:
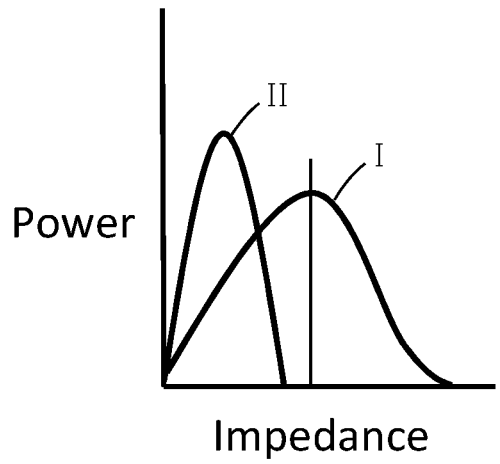
FIG. 6 is graphing of theoretical impedance (x-axis)/power (y-axis) curves.

In certain embodiments, the inventive subject matter is directed to systems and methods for modulating the form of energy delivered through one or more active electrodes associated with an instrument and/or modulating the aggregate surface area of operational return electrodes (bipolar and monopolar). These can be achieved through a set of computer executable instructions stored in volatile or non-volatile memory associated with the instrument. The instructions can be executed by a computer processor associated with an ECU 11 that is coupled to the instrument. Looking at FIGS. 6 and 7, first and second theoretical graphs of Power (Y-axis)/Impedance (X-axis) are shown. Higher powers means the active electrode will be more effective at delivering energy to tissue for an intended surgical effect, such as cutting or coagulating. In FIG. 6, curve I shows how power varies with impedance in a relative broad bell-shaped curve. This curve indicates how power would vary for some common ESUs. Curve II represents a power profile for a more specialized ESU. This represents a profile where peak power is in a narrow band. Power quickly falls off as impedance increases or decreases. This profile could be used where the peak power corresponds to tissue type having an inherent impedance under the peak. This profile therefore allows for a self-limiting effect on tissue. For example, it could be used to coagulate bloody, ulcerous tissue. As the tissue is coagulated, its impedance quickly increases and power drops, which prevents damage to tissue surrounding the target tissue.

Figure 7:
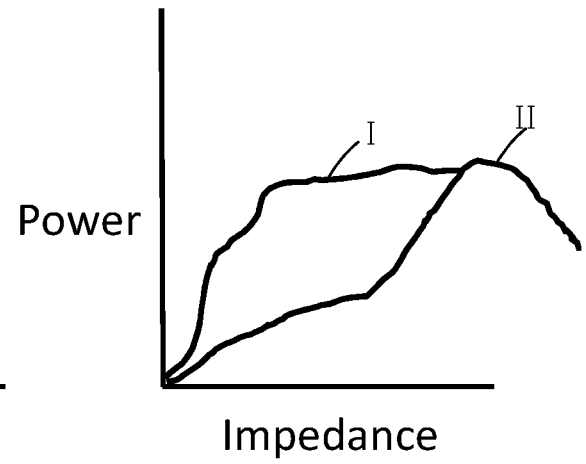
FIG. 7 is graphing of other theoretical impedance (x-axis)/power (y-axis) curves.

Turning to FIG. 7, a first curve I represents a sometimes desirable flat power curve for working with a broad range of tissues where defined power output can be maintained across a range of impedances corresponding to the varying impedances of different kinds of tissues. A second curve II represents a selected peaking of power at a defined impedance. In this example, the peak power is at relatively high impedance generally corresponding to the impedance of fatty tissue, such as is encountered during liposuction. This allows the system to selectively disrupt fatty tissue relative to other kinds of tissue. In other words, there is a high coupling efficiency between the power profile and the target tissue. Accordingly, the selectivity allows for less power delivery to lower impedance, non-target tissues, such as veins, arteries and muscle. Such tissues are therefore better protected from accidental trauma.

Various ECU systems may be used to create desired power profiles. For example, some known ECUs provide three output terminals, with one of the terminals being an energizable terminal for conveying energy, e.g., RF energy, to an energizable element of a handpiece. Such an ECU is usually configured to energize the energizable terminal when a circuit between the two remaining output terminals is completed, as through the closing of a user-actuated switch or an automatically programmed switch. In some embodiments discussed herein, a programmed switch operates depending on predefined temperature limits for the points on the instrument and/or patient target area.

Known ECUs include those manufactured by Ellman International, such as those under the brand SURIGTRON and described in U.S. Pat. No. 6,652,514, the contents of which are incorporated herein by reference in their entirety. The SURGITRON provides a three-wire output connector for powering and controlling electrosurgical handpieces. Conventional ECUs can generate, for example, one or more radio-frequency (RF) modulated waveforms, e.g., at a frequency of about 4 megahertz (MHz), which can be delivered to a target site by way of an electrosurgical handpiece having an energizable electrode defining an active surface. ECUs configured for both monopolar and bipolar operations have been developed by the assignee of this application and are disclosed in U.S. Pat. No. 7,479,140, the contents of which are incorporated herein by reference in their entirety, In some cases, the active surface of an electrosurgical system can be configured for ablative and/or non-ablative electrosurgery. As used herein, an ablative procedure is one where the electrode and power settings result in cutting, coagulation, vaporization or other such traumatic disruption to the integrity of treated tissue, and a non-ablative procedure is one where such cutting, coagulation, vaporization or other such traumatic disruption to the integrity of treated tissue does not result. An electrosurgical instrument can be configured provide a given combination of operating parameters suitable for achieving a desired therapeutic outcome based on a user's selection of therapeutic outcome and, for example, configuration of energizable electrode. Some electrosurgical instruments are configured to recognize a configuration or type of energizable electrode automatically.

A typical instrument configured for use in the surgical market segment delivers a peak output power of about 300 watts RMS (e.g., between about 290 Watts RMS and about 310 Watts RMS) in a cutting mode, and a lower peak power corresponding to each of a coagulate and fulgurate modes. A typical instrument configured for use in the aesthetic market segment delivers a peak output power of about 400 watts RMS (e.g., between about 385 Watts RMS and about 415 Watts RMS) in an "aesthetic mode" (e.g., skin tightening), about 300 Watts RMS in a surgical cutting mode and a lower peak power corresponding to each of a coagulate and fulgurate mode.

As used herein an "electrosurgical treatment mode" means a distinct configuration of an electrosurgical instrument corresponding to a distinct perceived result arising from a given user input. Each distinct configuration can correspond to a physical configuration, a software configuration, a firmware configuration, or a combination thereof.

In some respects, general functional characteristics of disclosed instruments can best be understood in the context of "electrosurgical treatment modes". In general, an electrosurgical mode is defined by a waveform comprising a given frequency, duty cycle, and amplitude (e.g., a maximum power output). Several representative examples of "modes" corresponding to respective therapeutic outcomes follow:

Cut—4 MHz and/or 400 kHz frequency, 90%-100% duty cycle sine wave at 300 watts RMS max power Blend 1—4 MHz and/or 400 kHz frequency, 25%-75% duty cycle sine wave at 250 watts RMS max power Coag/Hemostasis—4 MHz and/or 400 KHz frequency, 10%-40% duty cycle sine wave at 200 watts RMS max power Fulgurate—4 MHz and/or 400 kHz frequency, very low duty cycle sine wave at 150 watts RMS max power Aesthetic Mode I—4 MHz and/or 400 kHz, 90%-100% duty cycle sine wave at 300 watts RMS max power Aesthetic Mode II—4 MHz and/or 400 kHz mixed frequency 90%-100% duty cycle sine wave at 300 watts RMS max power Bipolar—4 Mhz and/or 400 kHz, 1.7 MHz, and/or 400 kHz frequency undetermined duty cycle sine wave at 100 watts RMS max power Each of the modes listed above except the Aesthetic Modes I & II is intended primarily for use in a surgical procedure. Aesthetic Modes I & II are modes intended primarily for use in aesthetic therapies. U.S. patent application Ser. No. 11/897,035, which is owned by the assignee of this patent application and is incorporated herein in its entirety, discloses an electrosurgical instrument configured to generate three carrier frequencies, four operating modes represented by different electrical modulation waveforms, and to combine each of the three carrier frequencies with any of the electrical modulation waveforms representing the different operating modes to form a unique set of electrosurgical currents, and to deliver such electrosurgical currents to either of a connected monopolar or bipolar handpiece or an instrument configured to offer both modes of operation.

As used herein "electrosurgical treatment mode" means a distinct configuration of an electrosurgical instrument corresponding to a distinct perceived result arising from a given user input. Each distinct configuration can correspond to a physical configuration, a software configuration, a firmware configuration, or a combination thereof.

U.S. patent application Ser. No. 11/897,035 teaches that operational modes include monopolar and/or bipolar activation, and a user selection of carrier frequency and modulating waveforms representing one of the four operating modes. Generally, the modulation frequencies will vary from 0 Hz to 35 KHz. Specifically, the four operating electrosurgical modes are represented by cutting: CW output with maximum (or 90%-100%) average power obtained with full-wave rectified and filtered carrier waveforms; cutting/coagulation: approximately 25%-75% average power output achieved with amplitude modulated or pulsed sine wave "with a pulse" frequency on the order of 100 to 5000 cps; hemostasis: approximately 10%-40% average power output achieved with amplitude modulated or pulsed sine wave with a "pulse" frequency on the order of 100 to 5000 cps with a lower duty cycle than seen on the cutting/coagulation mode; fulgurate (or Spark-Gap Wave): approximately 20% average power output achieved with very short repeating bursts of high voltage energy, with on the order of 100 to 5000 cps. The percentages given are with respect to the maximum value.

The various combinations of carrier frequency and modulation combined with the choice of handpiece selected by the user/surgeon produces a remarkable number of active electrosurgical currents with a wide variety of tissue effects. Three different carriers each with four different modulations applicable to tissue via either of two different handpieces provides a total of 12 different electrosurgical currents via the two handpieces and provides, in essence, at selected power levels varied levels of coagulation and cutting. This includes not only the usual high power tissue cutting currents, as well as low power bleeder coagulation currents but also more modest tissue effects with controllable lateral heat spread better suited around critical anatomical parts for hemostasis, as well as lower frequency currents for application to liquid-heavy surgical procedures. While, generally speaking, the monopolar operation is preferred for smooth cutting and combined cutting and coagulation, whereas bipolar operation concentrates the electrosurgical currents between the active and return electrodes, and is thus preferred for local hemostasis with lower power, many surgical situations may arise where it is preferred that higher power electrosurgical currents are applied with the bipolar operation and lower power electrosurgical currents with the monopolar operation.

In some embodiments, the first carrier frequency is in the range of about 3.8-4.0 MHz or thereabout, the second carrier frequency is in the range of about 1.7-2.0 MHz or thereabout, and the third carrier frequency is in the range of about 400-600 KHz or thereabout. In some embodiments, the values are 4 MHz or thereabout, 1.71 MHz or thereabout, and 500 KHz or thereabout.

In some embodiments, the first, second and third carrier frequencies are derived by division by 2 upon selection from RF carrier generators at double the desired frequencies which simplifies the RF generator selection circuitry.

The foregoing are non-limiting, representative RF and other power profile parameters. Other such parameters can be employed depending on application needs.

The names and/or specifications for the individual modes described herein are merely exemplary in nature and can vary from those presented herein. For example, some instruments described herein are software or firmware programmable. Such instruments allow a given hardware configuration to be tailored to specific market segments, or end uses. For example, a user, a manufacturer, a distributor, a reseller, etc., may define particular waveforms, or modes, in correspondence to a selected therapeutic outcome. As but one example, a given waveform might be relatively more suitable for cutting a first type of tissue than another waveform, whereas the other waveform might be relatively more suitable for cutting a second type of tissue. Instruments as disclosed herein can be programmed with one or the other waveforms to correspond to an end-user's preferred use (e.g., one end-user might be more likely to cut the first type of tissue, so an instrument provided to that end user can be programmed to provide the corresponding more effective waveform when a "cut" function is selected).

Such market-segment differentiation using the same base hardware can permit a manufacturer to enjoy economies of scale during production, while also being able to supply each distinct market segment with suitable, competitive product.

As used herein, "and/or" means "and" or "or", as well as "and" and "or." Moreover, any and all patent and non-patent literature cited herein is hereby incorporated by references in its entirety for all purposes.

The principles described above in connection with any particular example can be combined with the principles described in connection with any one or more of the other examples. Accordingly, this detailed description shall not be construed in a limiting sense, and following a review of this disclosure, those of ordinary skill in the art will appreciate the wide variety of systems that can be devised using the various concepts described herein. Moreover, those of ordinary skill in the art will appreciate that the exemplary embodiments disclosed herein can be adapted to various configurations without departing from the disclosed principles.

The previous description of embodiments is provided to enable any person skilled in the art to make or use the disclosed innovations. Various modifications to those embodiments will be readily apparent to those skilled in the art from the teachings herein, and the generic principles defined herein may be applied to other embodiments without departing from the spirit or scope of this disclosure. Thus, the claimed inventions are not intended to be limited to the embodiments shown herein, but are to be accorded the full scope consistent with the language of the claims. In the claims reference to an element in the singular, such as by use of the article "a" or "an" is not intended to mean "one and only one" unless specifically so stated, but rather "one or more".

All structural and functional equivalents to the elements of the various embodiments described throughout the disclosure that are known or later come to be known to those of ordinary skill in the art are intended to be encompassed by the features described and claimed herein. Moreover, nothing disclosed herein is intended to be dedicated to the public regardless of whether such disclosure is explicitly recited in the claims. No claim element is to be construed as "a means plus function" claim under US patent law, unless the element is expressly recited using the phrase "means for" or "step for".

The inventor reserves all rights to the subject matter disclosed herein, including the right to claim all that comes within the scope and spirit of the following claims:

The invention claimed is:

1. An electrosurgical system, comprising:
   a working portion with an electrode configuration that operates in a bipolar mode and has an active electrode and a plurality of return electrodes, each return electrode being separately addressable from each other return electrode and the active electrode, wherein at least one of the separately addressable return electrodes is continuously operable to maintain an activated current path with the active electrode, and at least one other separately addressable return electrode is selectively activatable to provide continuous control of an aggregate surface area of the return electrodes in service and thereby to provide continuous control of a current density applied in or over a target area;
   the electrosurgical system configured to deliver a peak power at a defined impedance corresponding to an impedance value of fatty tissue; and
   wherein the power decreases as impedance either increases or decreases relative to the defined impedance, thereby providing a self-limiting effect on an adjacent tissue type different than fat tissue.

2. The electrosurgical system of claim 1 wherein the plurality of return electrodes comprises a set of two or more return electrodes that can be selectively engaged into operation to control a temperature at one or more electrodes in the set of two or more return electrodes.

3. The electrosurgical system of claim 2 wherein each of at least two return electrodes in the set of two or more return electrodes can be separately engaged into operation relative to at least one other return electrode in the set.

4. The electrosurgical system of claim 2 wherein one or more temperature sensors is associated with each return electrode.

5. The electrosurgical system of claim 4 wherein each separately addressable return electrode is associated with a separately readable temperature sensor.

6. The electrosurgical system of claim 5 further comprising circuitry for switching at least one electrode automatically into or out of service in correspondence with a plurality of predefined parameters, at least one of the parameters being a temperature reading in proximity to at least one return electrode.

7. The electrosurgical system of claim 2, wherein the electrode configuration comprises a first electrode configuration, the system further comprising a second electrode configuration that operates in a monopolar mode, a return electrode that is separate from the instrument and usable in the monopolar mode of operation.

8. The electrosurgical system of claim 1 further comprising an ECU and a corresponding controller, wherein each electrode in the electrode configuration is in communication with the controller.

9. The electrosurgical system of claim 1 further comprising a shaft defining a lumen and a valve assembly couplable to a suction source, which becomes in fluid communication with the lumen.

10. The electrosurgical system of claim 1 wherein the system is configured to activate or deactivate one or more return electrodes depending on readings from one or more temperature sensors associated with the one or more return electrodes or the target area.

11. The electrosurgical system of claim 1 wherein the system further comprises a processor and a storage medium with stored executable instructions that, when executed, cause the processor to control one or more of a frequency, a power, a waveform, and a duty cycle of RF energy input though the active electrode in correspondence with a desired electrosurgical operation mode.

12. The electrosurgical system of claim 11 wherein the system is configured to modulate heating at return electrodes by modulating duty cycles for the operation of the electrodes, the modulation being based on readings from one or more temperature sensors in the system.

13. The electrosurgical system of claim 1 wherein the system is configured to activate one or more return electrodes into service as a temperature limit is sensed by one or more temperature sensors.

14. The multimode electrosurgical system of claim 1, wherein the instrument includes a second working portion comprising one or more of the plurality of return electrodes, the system being configured so that the active electrode provides an ablative thermal treatment effect at a first target area and one or more of the return electrodes are controllable to provide a non-ablative thermal effect at a second target area spaced apart from the first target area while the active electrode is at the first target area.

15. The multimode electrosurgical system of claim 14, wherein the system is configured to activate or deactivate one or more return electrodes into or out of service as a temperature limit is sensed by one or temperature sensors disposed on the instrument so as to monitor the temperatures at the second target area.

16. The multimode electrosurgical system of claim 15, wherein the system is configured to selectively disrupt fatty tissue relative to other kinds of tissue through the active electrode when the instrument is in fatty tissue at the first target area and to provide the non-ablative thermal effect on tissue at the second target area.

17. The multimode electrosurgical system of claim 1, wherein the system is configured with selectivity that allows for less power delivery to lower impedance, non-target, non-fatty tissues, namely veins and arteries, and wherein a second mode of the electrosurgical system is configured to concurrently maintain a layer of tissue adjacent the fatty tissue at a selected temperature while effecting disruption of the fatty tissue.

18. The multimode electrosurgical system of claim 1, wherein at least one of the return electrodes has a surface operably orientable towards a tissue type different than fatty tissue when the active electrode is operably oriented toward a fatty tissue layer.

19. The multimode electrosurgical system of claim 18, wherein the working portion comprises a cannula defining at least one lumen, the active electrode being disposed at the distal end of the cannula and the return electrodes being spaced from the active electrode and disposed on the surface of the cannula, in line with its longitudinal axis, the arrangement of active and return electrodes defining a current path for the non-ablative heating of the different tissue adjacent the fatty tissue while the active electrode is operated in an ablative mode.

20. The multimode electrosurgical system of claim 19, wherein the active electrode comprises a ring-shaped electrode disposed on the distal tip of the cannula.

21. A multimode electrosurgical system, comprising an electrosurgical instrument, the instrument having a working portion with an electrode configuration that operates in a bipolar mode and has an active electrode and a plurality of return electrodes, each return electrode being separately addressable, wherein at least one of the separately addressable return electrodes is continuously operable to maintain an activated current path with the active electrode and at least one other separately addressable return electrode is selectively activatable to provide continuous control of an aggregate surface area of the return electrodes in service and thereby to provide continuous control of a current density applied to a target area, the electrosurgical system configured to deliver a peak power at a defined impedance corresponding to an impedance value of fatty tissue contained in the target area, and wherein the power decreases as impedance either increases or decreases relative to the defined impedance, thereby providing a self-limiting effect on a tissue type different than fatty tissue wherein the electrode configuration comprises a first electrode configuration, the system further comprising a second electrode configuration that operates in a monopolar mode, a return electrode separate from the instrument and usable in the monopolar mode of operation against a patient's body.

22. The system according to claim 21, further comprising circuitry configured to selectively activate the return electrode operable in the monopolar mode as a temperature limit is sensed by one or more temperature sensors.

23. A method of liposuction and skin tightening comprising inserting a working portion of an instrument in or over a target area comprising subdermal fatty tissue, the working portion having an active electrode and at least two return electrodes, at least one of the return electrodes having a surface being oriented towards a dermal layer when the active electrode is oriented toward the fatty tissue, wherein at least one of the return electrodes is configured to be continuously operable to maintain an activated current path with the active electrode, and at least one other return electrode is configured to selectively activate and deactivate to provide continuous control of an aggregate surface area of the return electrodes, the return electrodes being selectively activatable from each other return electrode and the active electrode; energizing the active electrode with a peak power at a defined impedance corresponding to an impedance value of fatty tissue contained in the subdermal fatty tissue adjacent the dermal layer, wherein the power decreases from the peak power as impedance either increases or decreases relative to the defined impedance, thereby providing a self-limiting effect on a tissue type different than fatty tissue; and controlling the temperature at epidermal tissue of the dermal layer within a range to effect skin tightening by selectively activating or deactivating the at least one other return electrode to control the aggregate surface area of the return electrodes and thereby to control a current density applied to the target area.

24. A method of disrupting fatty tissue in a target area of a patient, the method comprising:
applying a working portion of an instrument in or over the target area, the working portion having an active electrode and a plurality of return electrodes that are capable of electrical contact with the target area, each return electrode being separately addressable from each other return electrode and the active electrode;
energizing the active electrode with a peak power at a defined impedance corresponding to an impedance value of fatty tissue in the target area, wherein the power decreases from the peak power as impedance either increases or decreases relative to the defined impedance, thereby providing a self-limiting effect on a tissue type different than fatty tissue;
monitoring a tissue temperature in the target area; and
maintaining the tissue temperature within a selected temperature range by selectively activating and/or deactivating any one or more of the return electrodes to vary an aggregate surface area of all return electrodes in a current path with the active electrode in response to the tissue temperature in the target area falling below a selected upper threshold temperature or exceeding a selected upper temperature threshold, respectively.

25. The method of claim 24 further comprising controlling one or more of a frequency, a power, a waveform, and a duty cycle of RF energy input though the active electrode in correspondence with a desired electrosurgical operation mode.

26. The method of claim 25 further comprising modulating heating at return electrodes by modulating duty cycles for the operation of the electrodes, the modulation being based on readings from one or more temperature sensors associated with the instrument.

27. A method of disrupting fatty tissue in a target area of a patient, comprising:
applying a working portion of an instrument in or over the target area comprising the patient's dermal layer, the working portion having an active electrode, a constant-service return electrode, and one or more return electrodes, each return electrode being separately addressable from each other return electrode and the active electrode, each of the active and return electrodes being capable of electrical contact with the target area;
energizing the active electrode with a peak power at a defined impedance corresponding to an impedance value of fatty tissue at the target area, wherein the power decreases from the peak power as impedance either increases or decreases relative to the defined impedance, thereby providing a self-limiting effect on a tissue type different than fatty tissue;
monitoring a tissue temperature in the target area; and
maintaining the tissue temperature within a selected temperature range by selectively activating and/or deactivating any one or more of the separately addressable return electrodes to vary an aggregate surface area of all return electrodes in a current path with the active electrode in response to the tissue temperature in the target area falling below a selected upper threshold temperature or exceeding a selected upper temperature threshold, respectively.

28. The method of claim 27 further comprising controlling one or more of a frequency, a power, a waveform, and a duty cycle of RF energy input though the active electrode in correspondence with a desired electrosurgical operation mode.

29. The method of claim 28 further comprising modulating heating at return electrodes by modulating duty cycles for the operation of the electrodes, the modulation being based on readings from one or more temperature sensors associated with the instrument.

* * * * *